(12) United States Patent
Aranda Hernandez et al.

(10) Patent No.: US 11,331,497 B2
(45) Date of Patent: *May 17, 2022

(54) CARDIAC SIGNAL T-WAVE DETECTION

(71) Applicants: Medtronic, Inc., Minneapolis, MN (US); UMC Utrecht Holding B.V., Utrecht (NL)

(72) Inventors: Alfonso Aranda Hernandez, Maastricht (NL); Berthold Stegemann, Kassel (DE); Marc A. Vos, Utrecht (NL); David J. Sprenkeler, Utrecht (NL)

(73) Assignees: Medtronic, Inc., Minneapolis, MN (US); UMC Utrecht Holding B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,551

(22) Filed: Aug. 4, 2020

(65) Prior Publication Data

US 2020/0359927 A1    Nov. 19, 2020

Related U.S. Application Data

(63) Continuation of application No. 16/000,037, filed on Jun. 5, 2018, now Pat. No. 10,772,525.

(51) Int. Cl.
*A61N 1/365* (2006.01)
*A61B 5/00* (2006.01)
(Continued)

(52) U.S. Cl.
CPC .......... *A61N 1/36507* (2013.01); *A61B 5/349* (2021.01); *A61B 5/7282* (2013.01);
(Continued)

(58) Field of Classification Search
CPC .. A61N 1/36507; A61N 1/3702; A61B 5/349; A61B 5/7282; A61B 5/021; A61B 5/7217; A61B 5/725
See application file for complete search history.

(56) References Cited

U.S. PATENT DOCUMENTS 5,792,065 A * 8/1998 Xue .......................... A61B 5/35
600/516
7,725,172 B2  5/2010 Rouw et al.
(Continued)

OTHER PUBLICATIONS

International Preliminary Report on Patentability from International Application No. PCT/US2019/035206, dated Dec. 17, 2020, 6 pp.
(Continued)

*Primary Examiner* — Catherine M Voorhees
(74) *Attorney, Agent, or Firm* — Shumaker & Sieffert, P.A.

(57) ABSTRACT

An example device for detecting one or more parameters of a cardiac signal is disclosed herein. The device includes one or more electrodes and sensing circuitry configured to sense a cardiac signal via the one or more electrodes. The device further includes processing circuitry configured to determine a representative signal based on the cardiac signal, the representative signal having a single polarity, and determine an end of a T-wave of the cardiac signal based on an area under the representative signal.

20 Claims, 10 Drawing Sheets

(51) Int. Cl.
  *A61B 5/349* (2021.01)
  *A61B 5/021* (2006.01)
  *A61N 1/37* (2006.01)
(52) U.S. Cl.
  CPC .............. *A61B 5/021* (2013.01); *A61B 5/725* (2013.01); *A61B 5/7217* (2013.01); *A61N 1/3702* (2013.01)

(56) References Cited

U.S. PATENT DOCUMENTS

| | | | |
|---|---|---|---|
| 8,886,296 | B2 | 11/2014 | Patel et al. |
| 8,914,106 | B2 | 12/2014 | Charlton et al. |
| 8,942,795 | B2 | 1/2015 | Gunderson et al. |
| 9,597,525 | B2 | 3/2017 | Cao et al. |
| 10,772,525 | B2* | 9/2020 | Aranda Hernandez ..................... A61B 5/349 |
| 2004/0220631 | A1 | 11/2004 | Burnes et al. |
| 2006/0116592 | A1 | 6/2006 | Zhou et al. |
| 2009/0318822 | A1 | 12/2009 | Qu et al. |
| 2011/0245700 | A1 | 10/2011 | Ghanem et al. |
| 2013/0035738 | A1 | 2/2013 | Karst et al. |
| 2016/0114168 | A1 | 4/2016 | Demmer et al. |
| 2016/0256063 | A1* | 9/2016 | Friedman ........... A61B 5/02455 |
| 2018/0028828 | A1 | 2/2018 | Cao et al. |
| 2019/0365267 | A1 | 12/2019 | Aranda Hernandez et al. |

OTHER PUBLICATIONS

Bashir, et al., "A template matched-filter based scheme for detection and estimation of t-wave alternans," Biomedical Signal Processing and Control, vol. 13, No. 1, p. 247-261, Sep. 2014.
Berger et al., "Beat-to-Beat QT Interval Variability," Circulation, Sep. 1997; 96(5), 1557-1565. doi:10.1161/01.CIR.96.5.1557.
Burattini et al., "Dependency of Exercise-Induced T-Wave Alternans Predictive Power for the Occurrence of Ventricular Arrhythmias from Heart Rate," Annals of Noninvasive Electrocardiology, Jul. 2015;20(4), pp. 345-354.
Chatterjee et al., "Real Time P and T Wave Detection from ECG using FPGA," Procedia Technology, vol. 4, p. 840-844, Dec. 2012.
Diem, et al., "Temporary disturbances of the QT interval precede the onset of ventricular tachyarrhythmias in patients with structural heart diseases" Pacing and Clinical Electrophysiology, Nov. 2002; 25: pp. 1413-1418.
Fei et al., "Shortening of the QT interval immediately preceding the onset of idiopathic spontaneous ventricular tachycardia," American Heart Journal Oct. 1995; 130: pp. 915-917.
Huikuri et al., "Abnormalities in beat-to-beat dynamics of heart rate before the spontaneous onset of life-threatening ventricular tachyarrhythmias in patients with prior myocardial infarction," Circulation, May 1996; 93:1836-1844.
International Search Report and Written Opinion of International Application No. PCT/US2019/035206, dated Jul. 19, 2019, 11 pp.
Krokhaleva et al., "Increased Nonalternans Repolarization Variability Precedes Ventricular Tachycardia Onset in Patients with Implantable Defibrillators. Pacing and Clinical Electrophysiology," Nov. 2015; 39(2), pp. 140-148.
Lenis et al. "Comparison of Baseline Wander Removal Techniques considering the Preservation of ST Changes in the Ischemic ECG: A Simulation Study," Computational and Mathematical Methods in Medicine, Jan. 2017, 14 pp.
Li, et al., "Poincare mapping: A potential method for detection of T-wave alternans," Procedia Environmental Sciences, vol. 8, p. 575-581, Nov. 2011.
Madeira et al., "New approach for T-wave peak detection and T-wave end location in 12-lead paced ECG signals based on a mathematical model," Medical Engineering and Physics, vol. 35, No. 8, Aug. 2013, 20 pp.
Manriquez, et al., "Multi-Lead T Wave End Detection Based on Statistical Hypothesis Testing," IFAC Proceedings Volumes, vol. 39, Aug. 2006, 6 pp.
Maury et al., "Feasibility of measurement of endocardial T wave alternans prior to onset of ventricular arrhythmias in ICDs (ETWAS study)," Archives of Cardiovascular Diseases Supplements. Apr. 2010; 2: pp. 62.
Mehta et a., "Development of SVM based classification techniques for the delineation of wave components in 12-lead electrocardiogram," Biomedical Signal Processing and Control, vol. 3, No. 4, p. 341-349, Oct. 2008.
Mehta et al., "Application of support vector machine for the detection of P- and T-waves in 12-lead electrocardiogram," Computer Methods and Programs in Biomedicine, vol. 93, No. 1, p. 46-60, Nov. 2008.
Millar et al., "Correlation between refractory periods and activation-recovery intervals from electrograms: effects of rate and adrenergic interventions," Circulation, Aug. 1985;72(6), pp. 1372-1379.
Nearing et al., "Crescendo in Depolarization and Repolarization Heterogeneity Heralds Development of Ventricular Tachycardia in Hospitalized Patients with Decompensated Heart Failure," Circ Arrhythm Electrophysiol., Feb. 2012; 5: pp. 84-90.
Nearing et al., "Progressive increase in complexity of T-wave oscillations herald ischemia-induced ventricular fibrillation," Circulation Research, Sep. 2002; 91: pp. 727-732.
Shenthar et al., "Prolonged Tpeak-end and Tpeak-end/QT ratio as predictors of malignant ventricular arrhythmias in the acute phase of ST-segment elevation myocardial infarction: A prospective case-control study," Heart Rhythm, Mar. 2015; 12: pp. 484-489.
Shusterman et al., "Upsurge in T-wave alternans and nonalternating repolarization instability precedes spontaneous initiation of ventricular tachyarrhythmias in humans," Circulation, Apr. 2006; 113: pp. 2880-2887.
Swerdlow et al., "Intracardiac Electrogram T-Wave Alternans/ Variability Increases Before Spontaneous Ventricular Tachyarrhythmias in Implantable Cardioverter-Defibrillator Patients: A Prospective, Multi-Center Study" Circulation, Jan. 2011; 123: pp. 1052-1060.
Vázquez-Seisdedos et al., "New approach for T-wave end detection on electrocardiogram: Performance in noisy conditions," BioMedical Engineering Online, vol. 10, No. 1, 11 pp., Sep. 2011.
Prosecution History from U.S. Appl. No. 16/000,037, dated Jan. 21, 2020 through Jul. 2, 2020, 51 pp.

* cited by examiner

CARDIAC SIGNAL T-WAVE DETECTION

This application is a continuation of U.S. patent application Ser. No. 16/000,037, filed Jun. 5, 2018, the entire content of which is incorporated herein by reference.

TECHNICAL FIELD

This disclosure relates to cardiac monitoring and, more particularly, to evaluation of features of cardiac signals.

BACKGROUND

Cardiac signal analysis may be performed by a variety of devices, such as implantable medical devices (IMDs) and external devices (e.g., smart watches, fitness monitors, mobile devices, Holter monitors, wearable defibrillators, or the like). For example, devices may be configured to process cardiac signals (e.g., cardiac electrograms (EGMs) and electrocardiograms (ECGs)) sensed by one or more electrodes. Features of cardiac signals may include the P-wave, Q-wave, R-wave, S-wave, QRS-complex, and T-wave. Accurate detection and delineation of features cardiac signals, such as T-waves, may be of importance for improving operation of devices.

Cardiac pacing is delivered to patients to treat a wide variety of cardiac dysfunctions. Cardiac pacing is often delivered by an 1 MB. An implantable cardioverter-defibrillator (ICD), for example, may provide pacing functionality and also provide cardioversion or defibrillation in response to detected cardiac tachyarrhythmias, if needed. However, pacemakers that do not provide anti-tachyarrhythmia shocks, and ICDs that do not deliver pacing therapy are also prevalent. An 1 MB typically delivers such therapy to the heart via electrodes located on one or more leads, which may be intracardiac or extracardiovascular leads, although leadless IMDs for delivering such therapies have also been implemented. Furthermore, leaded and leadless cardiac monitors that do not deliver therapy have also been implemented.

Patients with heart failure may be treated with cardiac resynchronization therapy (CRT). CRT is a form of cardiac pacing. The ventricles of some heart failure patients contract in an uncoordinated, or asynchronous, manner, which greatly reduces the pumping efficiency of the ventricles. CRT delivers pacing pulses at particular times, e.g., atrio-ventricular (A-V) intervals and/or intra-ventricular (V-V) intervals, and particular locations, e.g., to one or both of the right and left ventricles, to re-coordinate the contraction of the ventricles. In some examples, CRT involves delivery of pacing pulses to both ventricles to synchronize their contraction. In other examples, CRT involves delivery of pacing pulses to one ventricle, such as the left ventricle, to synchronize its contraction with that of the right.

SUMMARY

In general, the disclosure is directed to devices and techniques for identifying one or more features and/or determining one or more parameters of a cardiac signal (e.g., EGM and/or ECG) of a patient. For example, the disclosure describes techniques for identifying the end of the T-wave, which may allow a more robust delineation of cardiac signal features. This improved identification of the end of the T-wave may, for example, allow determination of variability of the activation recovery interval (ARI), e.g., a QT interval or interval measured from the start of the QRS complex to the end of the T-wave, which may enable predicting whether a patient is experiencing or will experience a tachyarrhythmia. In some examples, an IMD may deliver therapy to the patient to terminate or prevent a predicted tachyarrhythmia, which therapy need not necessarily include an anti-tachyarrhythmia shock. Signal processing techniques that may be used by processing circuitry, e.g., of the IMD, to delineate the one or more features may include, for example, determining an area under the curve of a representative signal, which may be generated from the cardiac signal by derivation and has a single polarity.

In one example, a device includes one or more electrodes, sensing circuitry configured to sense a cardiac signal via the one or more electrodes, and processing circuitry configured to determine a representative signal based on the cardiac signal, the representative signal having a single polarity, and determine an end of a T-wave of the cardiac signal based on an area under the representative signal.

In another example, a method includes sensing a cardiac signal. The method further includes determining a representative signal based on the cardiac signal, the representative signal having a single polarity, and determining an end of a T-wave of the cardiac signal based on an area under the representative signal.

In another example, a non-transitory, computer-readable storage medium storing a set of instructions that, when executed, cause a system to sense a cardiac signal of a patient. The computer-readable storage medium may further cause the system to determine a representative signal based on the cardiac signal, the representative signal having a single polarity, and determine an end of a T-wave of the cardiac signal based on an area under the representative signal.

In another example, a device includes one or more electrodes and sensing circuitry configured to sense a cardiac signal via the one or more electrodes. The device further includes processing circuitry configured to determine an end of a QRS complex of the cardiac signal, set a time window of the cardiac signal after the end of the QRS complex, determine a representative signal based on the cardiac signal and the time window, wherein the representative signal includes a square of a gradient of the cardiac signal within the window, and determine an end of a T-wave of the cardiac signal based on an area under the representative signal, wherein the end of the T-wave is given by a time in which the area under the representative signal is approximately equal to a threshold portion of a total area under the representative signal.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
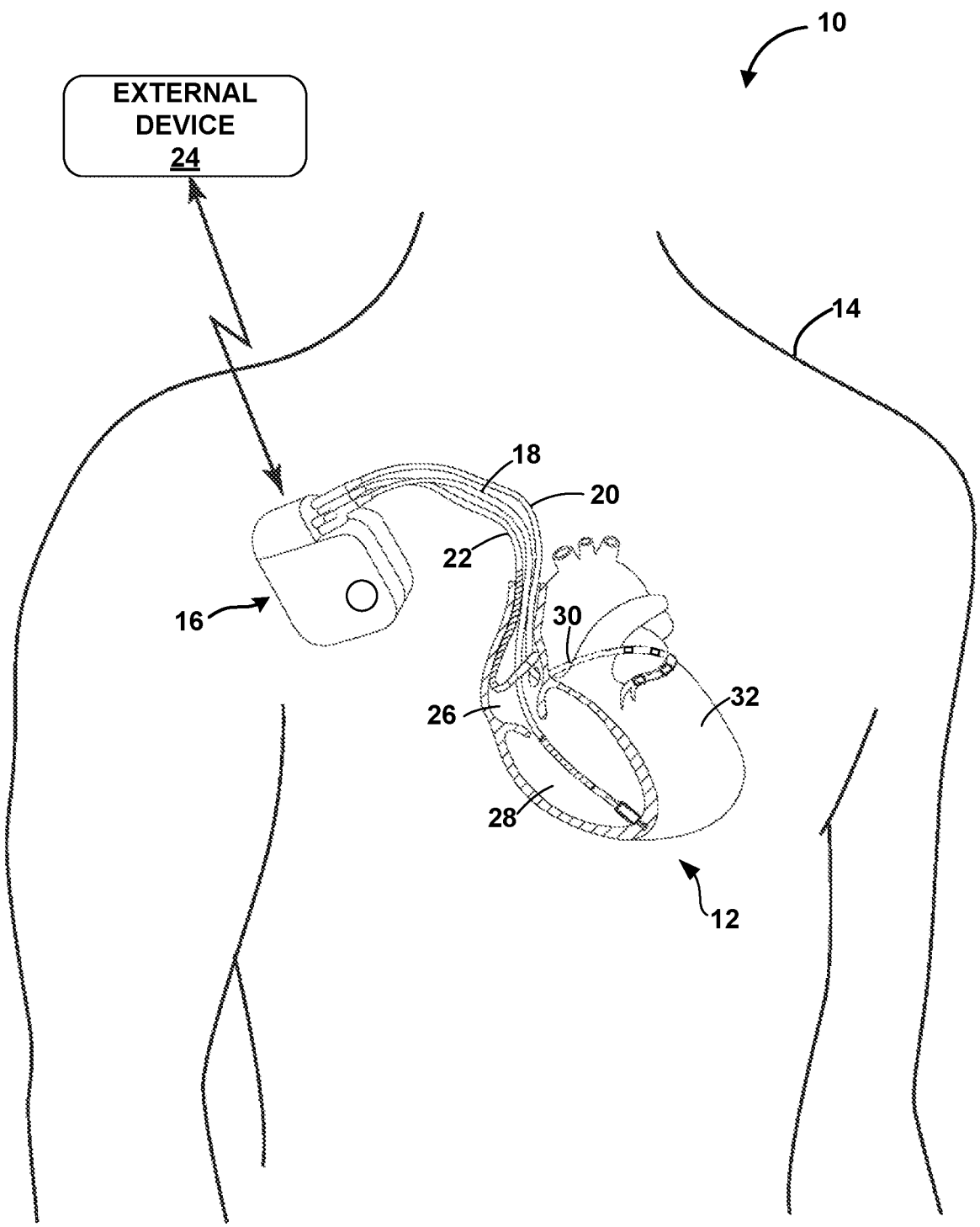
FIG. 1 is a conceptual diagram illustrating an example system for monitoring and treating cardiac events, which may be used to identify one or more parameters of a cardiac electrogram (EGM).

This disclosure describes techniques for identifying one or more parameters of a cardiac signal, such as end times of the QRS complex and T-wave. The parameters may be used to, for example, detect or predict arrhythmias, to evaluate other conditions of the patient, or to configure and/or evaluate therapies, such as CRT.

In some examples, IMDs may deliver therapy to a patient based on observable events (e.g., a tachyarrhythmia) of a sensed cardiac EGM. Although some therapies such as defibrillation shocks may restore the patient's heart to normal function after a tachyarrhythmia is detected, defibrillation shocks may be painful to the patient and cause permanent damage to the patient's cardiac tissue. In some cases, the patient may require hospitalization following the delivery of a defibrillation shock. For at least these reasons, it may be beneficial to improve an accuracy in which an IMD detects the presence of an arrhythmia in the patient, e.g., by increasing an accuracy of the one or more parameters of the cardiac EGM measured by the IMD. Furthermore, it may be beneficial to predict tachyarrhythmia before it occurs and deliver therapy (such as pacing) to prevent the tachyarrhythmia, rather than shocks to terminate an occurring tachyarrhythmia.

Techniques of this disclosure may increase the accuracy with which processing circuitry identifies one or more parameters of a cardiac signal acquired by a device, such as, for example, start and/or end times of one or more features of a cardiac signal (e.g., P-wave start time, P-wave end time, QRS complex start time, QRS complex end time, T-wave start time, and T-wave end time), which may allow for more accurate delineation of these features. In some examples, the processing circuitry may determine representative signals of the cardiac signal by performing signal processing methods including but not limited to filtering the cardiac signal, calculating the gradient of the cardiac signal, and amplifying the cardiac signal. The processing circuitry may determine an end time of a QRS complex of the cardiac signal and an end time of the subsequent T-wave in the cardiac signal based on areas under the representative signals calculated by the device. T-wave end times determined according to the techniques described herein may be used to, for example, determine short-term variability (STV) of the activation recovery interval (ARI), which may in turn be used to predict tachyarrhythmia and or determine whether CRT will be effective, as examples.

In some examples, the techniques of this disclosure may enable identification of end times that accurately reflect times in which the corresponding events occurred in the heart by processing circuitry using a cardiac EGM acquired by an IMD, rather than an electrocardiogram (ECG). Furthermore, the computational complexity of the techniques described herein may be appropriate for implementation by processing circuitry of an IMD. In other examples, the techniques of this disclosure may enable accurate identification of features of an ECG acquired by an external device, such as but not limited to a smart watch, a fitness monitor, a mobile device, a Holter monitor, or a wearable defibrillator.

FIG. 1 is a conceptual diagram illustrating an example system 10 for monitoring and treating cardiac events, which may be used to identify one or more parameters of a cardiac electrogram (EGM). As illustrated by example system 10 in FIG. 1, a system for identifying one or more parameters of the cardiac EGM according to the techniques of this disclosure may include an IMD 16, which in the illustrated example is an ICD with pacing capabilities. IMD 16 is connected to leads 18, 20 and 22 and is communicatively coupled to external device 24. IMD 16 senses electrical signals attendant to the depolarization and repolarization of heart 12, e.g., an EGM, via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation pulses. IMD 16 may monitor EGM signals collected by electrodes on leads 18, 20 or 22, and based on the EGM signal, diagnose and treat cardiac episodes.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, external device 24 takes the form of a handheld computing device, computer workstation or networked computing device that includes a user interface for presenting information to and receiving input from a user. A user, such as a physician, technician, surgeon, electrophysiologist, or other clinician, may interact with external device 24 to retrieve physiological or diagnostic information from IMD 16. A user may also interact with external device 24 to program IMD 16, e.g., select values for operational parameters of the IMD. External device 24 may include processing circuitry configured to evaluate EGM signals transmitted from IMD 16 to external device 24.

IMD 16 and external device 24 may communicate via wireless communication using any techniques known in the art. Examples of communication techniques may include, for example, low frequency or radiofrequency (RF) telemetry, or according to the Bluetooth® or Bluetooth LE specifications. In some examples, external device 24 may be located remotely from IMD 16 and communicate with IMD 16 via a network.

System 10 of FIG. 1 is an example of a system for identifying one or more parameters of a cardiac EGM according to the techniques of this disclosure. In some examples, processing circuitry of one or both of IMD 16 and external device 24 includes cardiac signal analysis circuitry configured to determine one or more parameters of a cardiac signal of patient 14. In one example, the cardiac signal includes a cardiac EGM sensed via one or more electrodes of IMD 16. A cardiac EGM is a signal representative of electrical activity of the heart, measured by electrodes implanted within the body, and often within the heart itself. For example, a cardiac EGM may include P-waves (depolarization of the atria), R-waves (depolarization of the ventricles), and T-waves (repolarization of the ventricles), among other events. Information relating to the aforementioned events, such as time separating one or more of the events, may be applied for a number of purposes, such as to determine whether an arrhythmia is occurring and/or predict whether an arrhythmia is likely to occur. Cardiac signal analysis circuitry, which may be implemented as part of processing circuitry of IMD 16 and/or external device 24, may perform signal processing techniques to extract information indicating the one or more parameters of the cardiac signal.

IMD 16 may be configured to determine a time representing a start of a QRS complex of the cardiac EGM, a time representing an end of the QRS complex, and a time representing an end of a subsequent T-wave. In one example, IMD 16 is further configured to determine the QT interval (an activation recovery interval (ARI)) as a time separating the start of the QRS complex and the end of the subsequent T-wave. Subsequently, IMD 16 may measure a plurality of QT intervals, each QT interval of the plurality of QT intervals corresponding to a heartbeat of a plurality of heartbeats. The plurality of QT intervals, and other parameters such as but not limited to T-wave duration and QRS duration, may predict an upcoming (e.g., occurring within about one minute to about five minutes from the prediction) arrhythmia in patient 14. In response to determining that an arrhythmia will occur in patient 14, IMD 16 may deliver therapy to heart 12 of patient 14 via one or more electrodes of leads 18, 20, and 22.

Although the techniques for identifying one or more parameters of the cardiac EGM according to the techniques of this disclosure are described herein primarily with reference to example system 10, the techniques may be performed by other systems that differ from example system 10. For example, systems for identifying the one or more parameters according to the techniques of this disclosure may include an IMD having different functionality than IMD 16, and may include more, fewer or different implantable cardiac leads than leads 18, 20 and 22. In some examples, systems for identifying the one or more parameters include more or fewer leads, do not include any intracardiac leads, or do not include any leads. Example IMDs that may implement the techniques of this disclosure in addition to the illustrated example of IMD 16 include extracardiovascular ICDs, transcatheter pacing systems, such as the Micra™ transcatheter pacing system commercially available from Medtronic plc, of Dublin, Ireland, and insertable cardiac monitors, such as the Reveal LINQ™ available from Medtronic plc.

Figure 2:
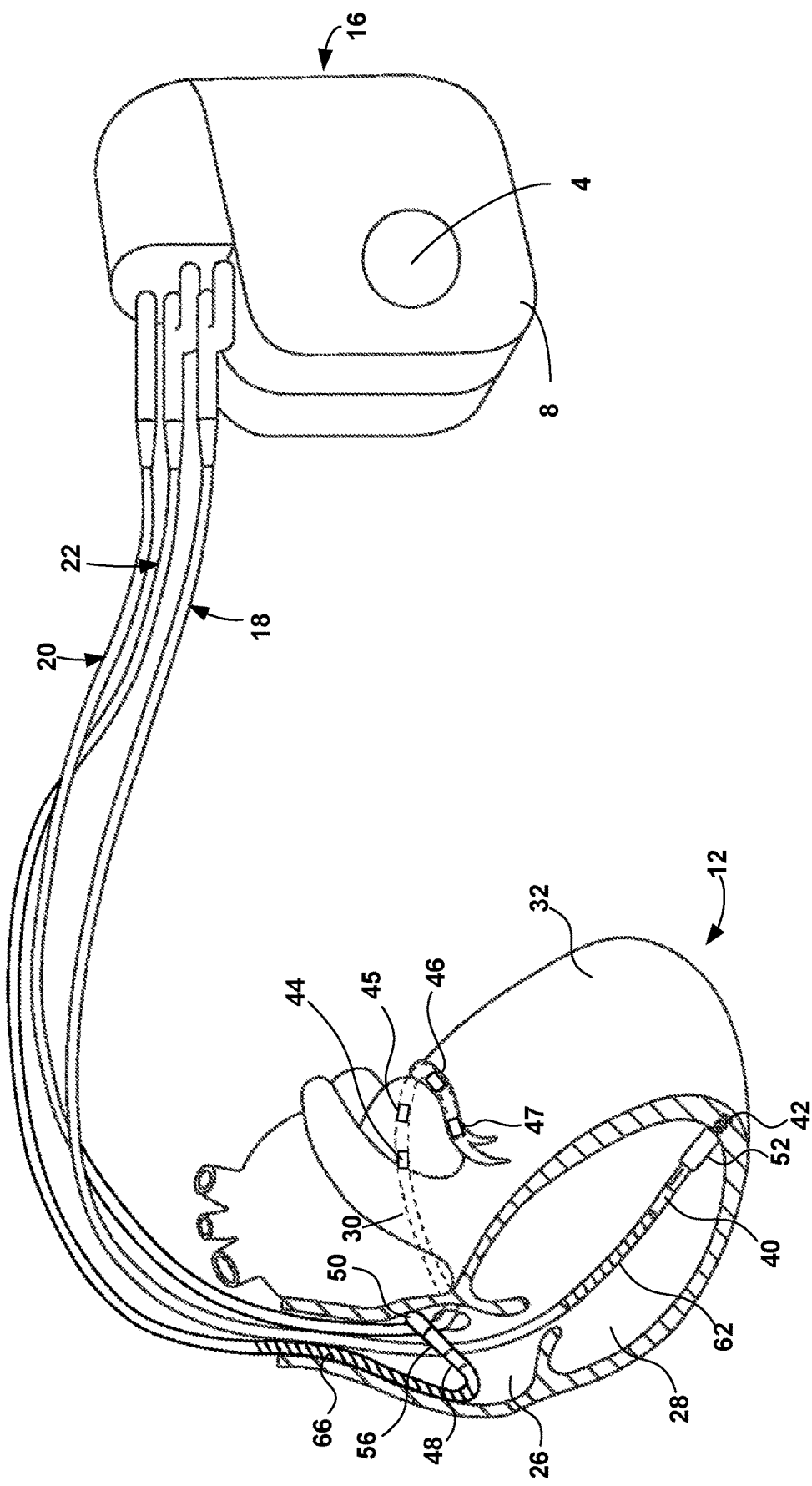
FIG. 2 is a conceptual diagram illustrating the IMD and leads of the system of FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 includes segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40, 44-47 and 48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 66, respectively, which may take the form of a coil. In some examples, each of electrodes 40, 42, 44-48, 50, 62, and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode includes substantially all of housing 8.

Housing 8 encloses signal generation circuitry that generates therapeutic stimulation, such as cardiac pacing, cardioversion and defibrillation pulses, as well as sensing circuitry for sensing electrical signals attendant to the depolarization and repolarization of heart 12. Housing 8 may also enclose a memory for storing the sensed electrical signals. Housing 8 may also enclose telemetry circuitry for communication between IMD 16 and external device 24.

IMD 16 senses electrical signals attendant to the depolarization and repolarization of heart 12 via electrodes 4, 40, 42, 44-48, 50, 62, and 66. IMD 16 may sense such electrical signals via any bipolar combination of electrodes 40, 42, 44-48, 50, 62, and 66. Furthermore, any of the electrodes 40, 42, 44-48, 50, 62, and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more extracardiovascular (e.g., epicardial, substernal, or subcutaneous) leads not positioned within the heart.

Figure 3:
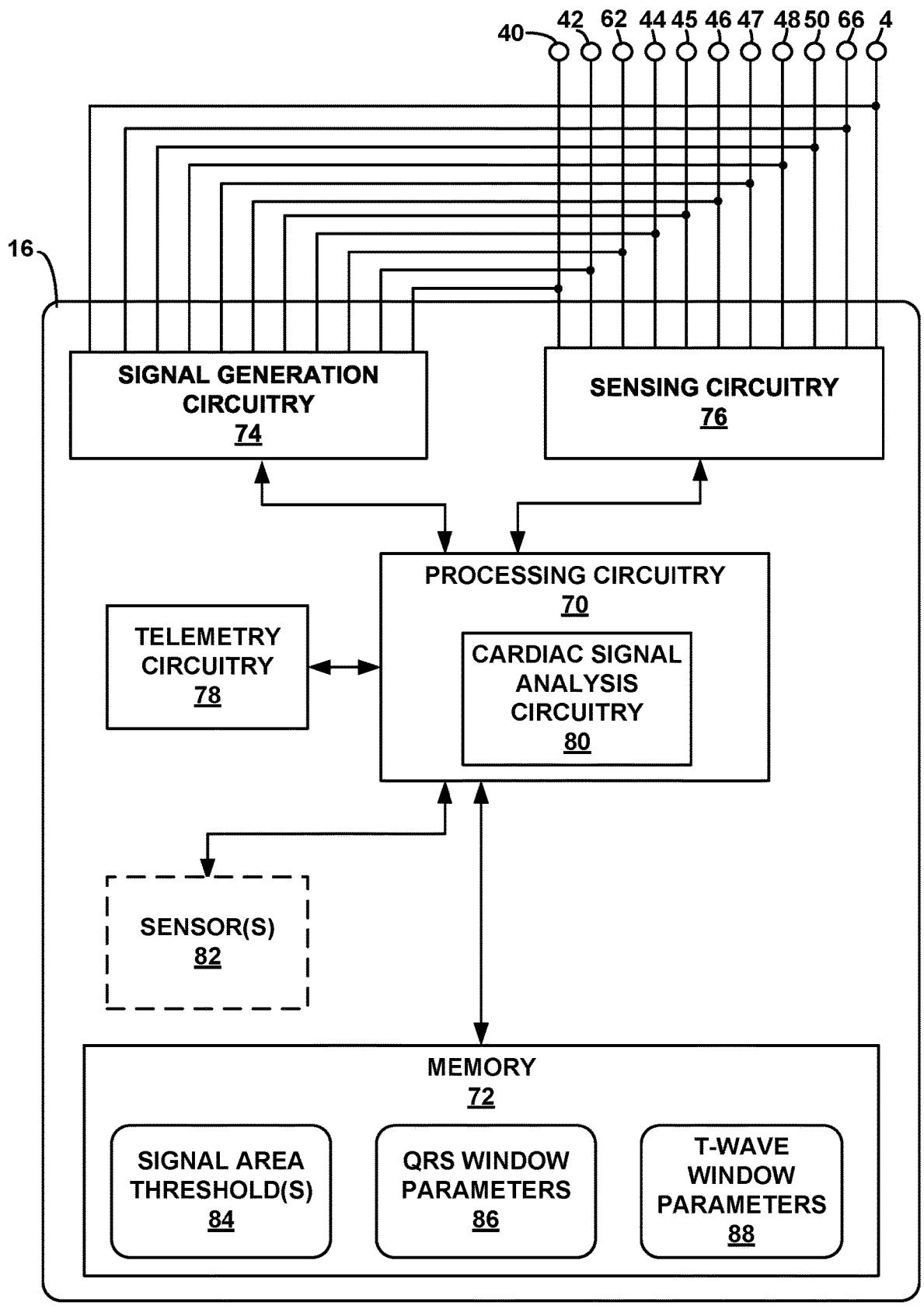
FIG. 3 is a block diagram illustrating an example configuration of an IMD for monitoring and treating cardiac events, which may be used to identify one or more parameters of the cardiac EGM.

FIG. 3 is a block diagram illustrating an example configuration of IMD 16 for monitoring and treating cardiac events, which may be used to identify one or more parameters of a cardiac EGM according to the techniques of this disclosure. In the illustrated example, IMD 16 includes processing circuitry 70, memory 72, signal generation circuitry 74, sensing circuitry 76, telemetry circuitry 78, cardiac signal analysis circuitry 80, and activity sensor 82. Memory 72 includes computer-readable instructions that, when executed by processing circuitry 70, cause IMD 16 and processing circuitry 70 to perform various functions attributed to IMD 16 and processing circuitry 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 70 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 70 may include multiple components, such as any combination of one or more microprocessors, one or more controllers, one or more DSPs, one or more ASICs, or one or more FPGAs, as well as other discrete or integrated logic circuitry. The functions attributed to processing circuitry 70 herein may be embodied as software, firmware, hardware or any combination thereof.

Generally, processing circuitry 70 controls signal generation circuitry 74 to deliver therapy to heart 12 of patient 14 according to selected values of one or more of therapy parameters, which may be stored in memory 72. As an example, processing circuitry 70 may control signal generation circuitry 74 to deliver electrical pulses with the amplitudes, pulse widths, frequency, and/or electrode polarities specified by the selected therapy parameter values. Parameters stored in memory 72 include thresholds or other conditions, which may be compared to parameters of the EGM, and based on which processing circuitry 70 controls signal generation circuitry 74 to deliver therapy, such as cardiac rates, intervals, and/or EGM morphology parameters.

Signal generation circuitry 74 is configured to generate and deliver electrical therapy to patient 14. As shown in FIG. 3, signal generation circuitry 74 is electrically coupled to electrodes 4, 40, 42, 44-48, 50, 62, and 66, e.g., via conductors of the respective leads 18, 20, and 22 and, in the case of housing electrode 4, within housing 8. For example, signal generation circuitry 74 may deliver pacing, defibrillation or cardioversion pulses to heart 12 via at least two of electrodes 4, 40, 42, 44-48, 50, 62 and 66. In some examples, signal generation circuitry 74 delivers therapy in the form of signals other than pulses such as sine waves, square waves, or other substantially continuous time signals.

Signal generation circuitry 74 may include one or more capacitors, charge pumps, current sources, or other signal generation circuitry. Signal generation circuitry 74 may also include switching circuitry (not shown) and processing circuitry 70 may use the switching circuitry to select, e.g., via a data/address bus, which of the available electrodes are used to deliver the electrical stimulation. The switching circuitry may include a switch array, switch matrix, multiplexer, or any other type of switching device suitable to selectively couple energy to selected electrodes.

Electrical sensing circuitry 76 monitors electrical cardiac signals from any combination of electrodes 4, 40, 42, 44-48, 50, 62 and 66. Sensing circuitry 76 may also include switching circuitry which processing circuitry 70 controls to select which of the available electrodes are used to sense the heart activity, depending upon which electrode combination is used in the current sensing configuration. In some examples, sensing circuitry 76 may include one or more amplifiers, filters, and analog-to-digital converters.

Sensing circuitry 76 may include one or more detection channels, each of which may include an amplifier. The detection channels may be used to sense cardiac signals, such as a cardiac EGM. Some detection channels may detect events, such as R-waves, P-waves, and T-waves and provide indications of the occurrences of such events to processing circuitry 70. One or more other detection channels may provide the signals to an analog-to-digital converter, for conversion into a digital signal for processing or analysis by processing circuitry 70 or cardiac signal analysis circuitry 80.

For example, sensing circuitry 76 may include one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processing circuitry 70 then uses that detection in measuring frequencies of the sensed events. In one example, at least one narrow band channel may include an R-wave or P-wave amplifier.

In some examples, sensing circuitry 76 includes a wide band channel which may include an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing circuitry 76 or processing circuitry 70. Processing circuitry 70 and cardiac signal analysis circuitry 80 may analyze the digitized version of signals from the wide band channel. Processing circuitry 70 may employ digital signal analysis techniques to characterize the digitized signals from the wide band channel to, for example, detect and classify the patient's heart rhythm.

Processing circuitry 70 may detect and classify the patient's heart rhythm based on the cardiac electrical signals sensed by sensing circuitry 76 employing any of the numerous signal processing methodologies known in the art. For example, processing circuitry 70 may maintain escape interval counters that may be reset upon sensing of R-waves by sensing circuitry 76. The value of the count present in the escape interval counters when reset by sensed depolarizations may be used by an episode classifier of processing circuitry 70 to measure the durations of R-R intervals, which are measurements that may be stored in memory 72. Processing circuitry 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processing circuitry 70 to determine whether the patient's heart 12 is presently exhibiting atrial or ventricular tachyarrhythmia.

In some examples, processing circuitry 70 may determine that tachyarrhythmia has occurred by identification of shortened R-R interval lengths. For example, processing circuitry 70 detects tachycardia when the interval length falls below a first threshold (e.g., 360 milliseconds (ms)) and fibrillation when the interval length falls below a second threshold (e.g., 320 ms). These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples. In some examples, an arrhythmia detection method may include any combination of suitable tachyarrhythmia detection algorithms. For example, EGM morphology may be considered in addition to or instead of interval length for detecting or predicting tachyarrhythmias.

Generally, processing circuitry 70 detects a treatable tachyarrhythmia, such as VF, based on the EGM, e.g., the R-R intervals and/or morphology of the EGM, and selects a therapy to deliver to terminate the tachyarrhythmia, such as an anti-tachycardia pacing regimen and/or defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase.

One or more sensors 82 may be optionally included in some examples of IMD 16. Sensors 82 may include one or more accelerometers. Sensors 82 may additionally or alternatively include other sensors such as a heart sounds sensor, a pressure sensor, a flow sensor, or an oxygen (02) saturation sensor. In some examples, processing circuitry 70 may detect respiration via a signal received from sensing circuitry 76 via one or more electrodes.

Information obtained from activity sensor 82 may be used to determine activity level, posture, blood pressure, blood flow, blood oxygen level, or respiratory rate, as examples. In some examples, this information may be used by IMD 16 to aid in the classification of an abnormal heart rhythm. In some examples, this information may be used by IMD 16 or a user of external device 24 to determine desired LV pacing locations and timings for delivery of CRT. For example, blood pressure or flow metrics may indicate the effectiveness LV pacing locations and timings in improving the performance of heart 12.

Sensors 82 may be located outside of the housing 8 of IMD 16. Sensors 82 may be located on a lead that is coupled to IMD 16 or may be implemented in a remote sensor that wirelessly communicates with IMD 16 via telemetry circuitry 78. In any case, sensors 82 are electrically or wirelessly coupled to circuitry contained within housing 8 of IMD 16.

In some examples, IMD 16 includes cardiac signal analysis circuitry 80. Cardiac signal analysis circuitry 80 and IMD 16 are configured to perform techniques for identifying one or more parameters of the cardiac EGM, as described herein. Cardiac signal analysis circuitry 80 may include software and/or firmware executed by processing circuitry 70. Additionally, or alternatively, cardiac signal analysis circuitry 80 may comprise certain circuitry of processing circuitry 70. According to some examples, sensing circuitry 76 senses a cardiac signal (e.g., cardiac EGM) via any combination of electrodes 4, 40, 42, 44-48, 50, 62, and 66 of IMD 16. As discussed above, sensing circuitry 76 may include a wideband amplifier, and sensing circuitry 76 may sense the cardiac signal with the wide-band sensing amplifier. In response to detecting or predicting an arrhythmia based on the one or more parameters identified by cardiac signal analysis circuitry 80, IMD 16 may deliver therapy pulses to patient 14. In one example, under the control of processing circuitry 70, signal generation circuitry 74 delivers therapy pulses to heart 12 via one or more of the electrodes, e.g., 40, 42, 44-48, 50, 62, and 66, of leads 18, 20, and 22.

Cardiac signal analysis circuitry 80 may include a microprocessor, a microcontroller, a DSP, an ASIC, an FPGA, or other equivalent discrete or integrated logic circuitry. Accordingly, cardiac signal analysis circuitry 80 may include any suitable structure, whether in hardware, software, firmware or any combination thereof, to perform the functions ascribed herein to cardiac signal analysis circuitry 80. In one example, cardiac signal analysis circuitry 80 receives a cardiac EGM via sensing circuitry 76, e.g., the wide band sensing channel of sensing circuitry 76, and any combination of electrodes 4, 40, 42, 44-48, 50, 62, and 66. Based on representative signals of the cardiac EGM, cardiac signal analysis circuitry 80 may measure a plurality of QT intervals of the cardiac EGM, each QT interval of the plurality of QT intervals representing a window of time between a start time of a QRS complex of the cardiac EGM, and an end time of a T-wave of the cardiac EGM (i.e., a window of time between the beginning of ventricular depolarization and the ending of ventricular repolarization). Additionally, or alternatively, cardiac signal analysis circuitry 80 may measure other parameters such as T-wave duration (window of time separating T-wave start time and T-wave end time), QRS duration, and heart rate.

Parameters (e.g., QRS end time, T-wave end time, QRS duration, T-wave duration, QT interval length, or the like) of the cardiac EGM measured by cardiac signal analysis circuitry 80 may indicate that an arrhythmia is imminent in patient 14. Hence, IMD 16 may perform analysis on parameters of the cardiac EGM to predict potential upcoming arrhythmia and deliver therapy to prevent the potential upcoming arrhythmia. In one example, IMD 16 may be configured to predict an upcoming arrhythmia between about one minute and about five minutes before an onset of the upcoming arrhythmia. After predicting the arrhythmia, IMD 16 may deliver therapy to heart 12 via signal generation circuitry 74. IMD 16 may deliver therapy via any combination of electrodes 40, 42, 44-48, 50, 62, and 66. IMD 16, as illustrated in FIG. 3, may accurately measure parameters of the cardiac EGM by producing determinations of QRS complex start times, QRS complex end times, and T-wave end times, among other parameters, that may be more accurate then determinations made by other techniques.

For example, cardiac signal analysis circuitry 80 may use a band-pass filter to create a filtered version of the EGM signal received from sensing circuitry 76. In one example, the band-pass filter may have a frequency pass range of 1 Hertz to 10 Hertz (e.g., the band pass filter attenuates frequency bands outside the frequency pass range), thus eliminating high-frequency and low-frequency noise in the cardiac EGM signal. In one example, noise may be introduced in the cardiac EGM signal by the respiratory system, the muscular system, the digestive system, the nervous system, and other systems in patient 14, as well as 60 Hertz noise or other external noise at any frequency from external sources such as medical equipment or other machinery. Cardiac signal analysis circuitry 80, or other components of IMD 16, may detect an occurrence of an R-wave (e.g., ventricular depolarization event) in the EGM. For example, sensing circuitry 76, e.g., a narrow band R-wave detection channel within the sensing circuitry, may provide an indication of the timing of R-wave detection to cardiac signal analysis circuitry 80. Cardiac signal analysis circuitry 80 may set a QRS window based on the detected R-wave, the QRS window starting at a first time relative to the R-wave and ending at a second time relative to the R-wave, the first time and the second time of the QRS window being QRS window parameters 86 stored in memory 72 of IMD 16. In some examples, the first time and the second time of the QRS window both occur after the R-wave. In other examples, at least one of the first time and the second time may occur before the R-wave.

In one example, the first time occurs 10 milliseconds after the R-wave, and the second time occurs 150 milliseconds after the R-wave. In other examples, the first time and the second time of the QRS window may include other values. IMD 16 may update QRS window parameters 86 in response to any of a variety of events. In some examples, IMD 16 may receive instructions from external device 24 to update QRS window parameters 86 (e.g., change the first time and the second time of the QRS window). Additionally, or alternatively, processing circuitry 70 of IMD 16 may automatically update QRS window parameters 86 in response to detecting a change in a heart rate of patient 14. For example, IMD 16 may decrease a length of the QRS window if the heart rate of patient 14 increases; and IMD 16 may increase the length of the QRS window if the heart rate of patient 14 decreases. In other examples, IMD 16 may update QRS window parameters 86 in response to other events, such as but not limited to signals from sensor(s) 82.

The QRS window may represent a period of time in which an end of the QRS complex is expected to occur. Hence, when determining the end of the QRS complex, IMD 16 may eliminate ("blank") portions of the filtered EGM outside of the QRS window. Additionally, IMD 16 may compute a gradient of the filtered EGM signal, the gradient being a derivative of the filtered EGM signal. A representative signal of the QRS complex may be calculated, the representative signal including the gradient of the filtered EGM signal. Additionally, or alternatively, the representative signal of the QRS complex may include an amplification of the gradient of the filtered EGM signal. In one example, the representative signal includes an exponential (e.g., square, cube, or the like) of the gradient of the filtered EGM signal. In one example, the representative signal may include a single polarity (e.g., the representative signal may be exclusively positive or exclusively negative, however, the representative signal may not alternate between positive and negative polarities). For instance, if the representative signal includes a square of the gradient of the filtered EGM signal, the square rectifies any negative portions of the representative signal, rendering the representative signal of the QRS complex to a single polarity. In other examples, IMD 16 may use a half-wave rectifier or a full-wave rectifier to create the representative signal having a single polarity. Additionally, or alternatively, IMD 16 may perform an absolute value function, a magnitude function, or the like to determine the representative signal having a single polarity.

Cardiac signal analysis circuitry 80 may determine an end of a QRS complex in the cardiac EGM signal based on an area under the representative signal of the QRS complex. In one example, cardiac signal analysis circuitry 80 is configured to compute a total area under the representative signal of the QRS complex. Additionally, cardiac signal analysis circuitry 80 is configured to calculate an area under any portion of the representative signal of the QRS complex, including any portion of the representative signal beginning at the first time of the QRS window and ending before the second time of the QRS window. Cardiac signal analysis circuitry 80 is configured to determine an end of a QRS complex as being an earliest determined time in which the area under the representative signal of the QRS complex is greater than or equal to a predetermined portion (e.g., threshold portion) of a total area under the representative signal of the QRS complex. In one example, the portion of the total area under the representative signal of the QRS complex is 0.9. In other words, cardiac signal analysis circuitry 80 determines the end of the QRS complex as being a first point within the QRS window in which the area under the representative signal of the QRS complex is greater than or equal to 90% of the total area under the representative signal. In other examples, the portion of the total area under the representative signal of the QRS complex indicating the end of the QRS complex may be greater or less than 0.9.

The portion of the total area under the representative signal of the QRS complex indicating the end of the QRS complex may be included within signal area threshold(s) 84 stored in memory 72 of IMD 16. In one example, IMD 16 may receive instructions from external device 24 to change signal area threshold(s) 84. In other examples, IMD 16 may update signal area threshold(s) 84 based on signals received from sensor(s) 82, processing circuitry 70, or cardiac signal analysis circuitry 80.

As discussed above, IMD 16 may detect an R-wave, and cardiac signal analysis circuitry 80 may set a QRS window based on the detected R-wave. Additionally, or alternatively, cardiac signal analysis circuitry 80 may set a T-wave window starting at a first time relative to the R-wave and ending at a second time relative to the R-wave, the first time and the second time of the T-wave window being T-wave window parameters 88 stored in memory 72 of IMD 16. In some examples, the first time of the T-wave window occurs at the QRS end time determined by cardiac signal analysis circuitry 80, and the second time of the T-wave window occurs 700 milliseconds after the R-wave. In other examples, the first time and the second time of the T-wave window may include other values. IMD 16 may update T-wave window parameters 88 based on any of a variety of events. In some examples, IMD 16 may receive instructions from external device 24 to update T-wave window parameters 88 (e.g., change the first time and the second time of the T-wave window). Additionally, or alternatively, processing circuitry 70 of IMD 16 may automatically update T-wave window parameters 88 in response to detecting a change in a heart rate of patient 14. For example, IMD 16 may decrease a length of the T-wave window if the heart rate of patient 14 increases; and IMD 16 may increase the length of the T-wave window if the heart rate of patient 14 decreases. In other examples, IMD 16 may update T-wave window parameters 88 in response to other events, such as but not limited to signals from sensor(s) 82.

The T-wave window may represent a period of time in which an end of the T-wave is expected to occur. Hence, when determining the end of the T-wave complex, IMD 16 may blank portions of the filtered EGM outside of the T-wave window (e.g., blanked portions may include the QRS complex preceding the T-wave, and a P-wave following the T-wave). Additionally, IMD 16 may compute a gradient of the filtered EGM signal, the gradient being a derivative of the filtered EGM signal. A representative signal of the T-wave may be determined, the representative signal including the gradient of the filtered EGM signal. Additionally, or alternatively, the representative signal may include an amplification of the gradient of the filtered EGM signal. In some examples, the representative signal includes an exponential (e.g., square, cube, or the like) of the gradient of the filtered EGM signal. In some examples, the representative signal may include a single polarity (e.g., the representative signal may be exclusively positive or exclusively negative, however, the representative signal may not alternate between positive and negative polarities). For instance, if the representative signal includes a square of the gradient of the filtered EGM signal, the square rectifies any negative portions of the representative signal, rendering the representative signal of the T-wave to a single polarity.

Cardiac signal analysis circuitry 80 may determine an end of a T-wave in the cardiac EGM signal based on an area under the representative signal of the T-wave. In one example, cardiac signal analysis circuitry 80 is configured to compute a total area under the representative signal of the T-wave. Additionally, cardiac signal analysis circuitry 80 is configured to calculate an area under any portion of the representative signal of the T-wave, including any portion of the representative signal beginning at the first time of the T-wave window and ending before the second time of the T-wave window. Cardiac signal analysis circuitry 80 is configured to determine an end of a T-wave as being an earliest determined time in which the area under the representative signal of the T-wave is greater than or equal to a predetermined portion (e.g., threshold portion) of a total area under the representative signal of the T-wave. In one example, the portion of the total area under the representative signal of the T-wave is 0.6. In other words, cardiac signal analysis circuitry 80 determines the end of the T-wave as being a first point within the T-wave window in which the area under the representative signal of the T-wave is equal to 60% of the total area under the representative signal. In other examples, the portion of the total area under the representative signal indicating the end of the T-wave may be greater or less than 0.6.

The portion of the total area under the representative signal indicating the end of the T-wave may be included within signal area threshold(s) 84 stored in memory 72 of IMD 16. In one example, IMD 16 may receive instructions from external device 24 to change signal area threshold(s) 84. In other examples, IMD 16 may update signal area threshold(s) 84 based on signals received from sensor(s) 82, processing circuitry 70, or cardiac signal analysis circuitry 80.

Cardiac signal analysis circuitry 80 may be further configured to measure one or more parameters of P-waves (e.g., atrial depolarization events). For example, cardiac signal analysis circuitry 80 may measure P-wave start time, P-wave end time, and P-wave duration, based on an area under a representative signal of the respective P-wave. Additionally, or alternatively, cardiac signal analysis circuitry 80 or processing circuitry 70 may measure P-R intervals (e.g., window of time separating P-wave start time and R-wave peak) and other intervals based on parameters measured using techniques of this disclosure. Cardiac signal analysis circuitry 80 may be configured calculate any combination of the derivative, integral, gradient, exponent, variance, amplitude, magnitude, and other mathematical operation of any portion of the cardiac EGM signal recorded by IMD 16.

Processing circuitry 70 and cardiac signal analysis circuitry 80 may be incorporated in a single processing unit. Cardiac signal analysis circuitry 80 may be a component of, or a software or firmware module executed by, processing circuitry 70.

Telemetry circuitry 78 includes any suitable hardware, firmware, software or any combination thereof for communicating with another device, such as external device 24 (FIG. 1). Under the control of processing circuitry 70, telemetry circuitry 78 may receive downlink telemetry from and send uplink telemetry to external device 24 with the aid of an antenna, which may be internal and/or external. In some examples, processing circuitry 70 may transmit cardiac signals, e.g., EGM signals, produced by sensing circuitry 76.

Processing circuitry 70 may also generate and store marker codes indicative of different cardiac or other physiological events detected by sensing circuitry 76, processing circuitry 70, or cardiac signal analysis circuitry 80 and transmit the marker codes to external device 24. Information which processing circuitry 70 may transmit to external device 24 via telemetry circuitry 78 may also include an indication of a change in disease state of the heart, an indication of a change in heart response to the therapy provided or an indication that the heart continues to response in the same (or similar) manner to the therapy provided. Such information may be included as part of a marker channel with an EGM.

Figure 4:
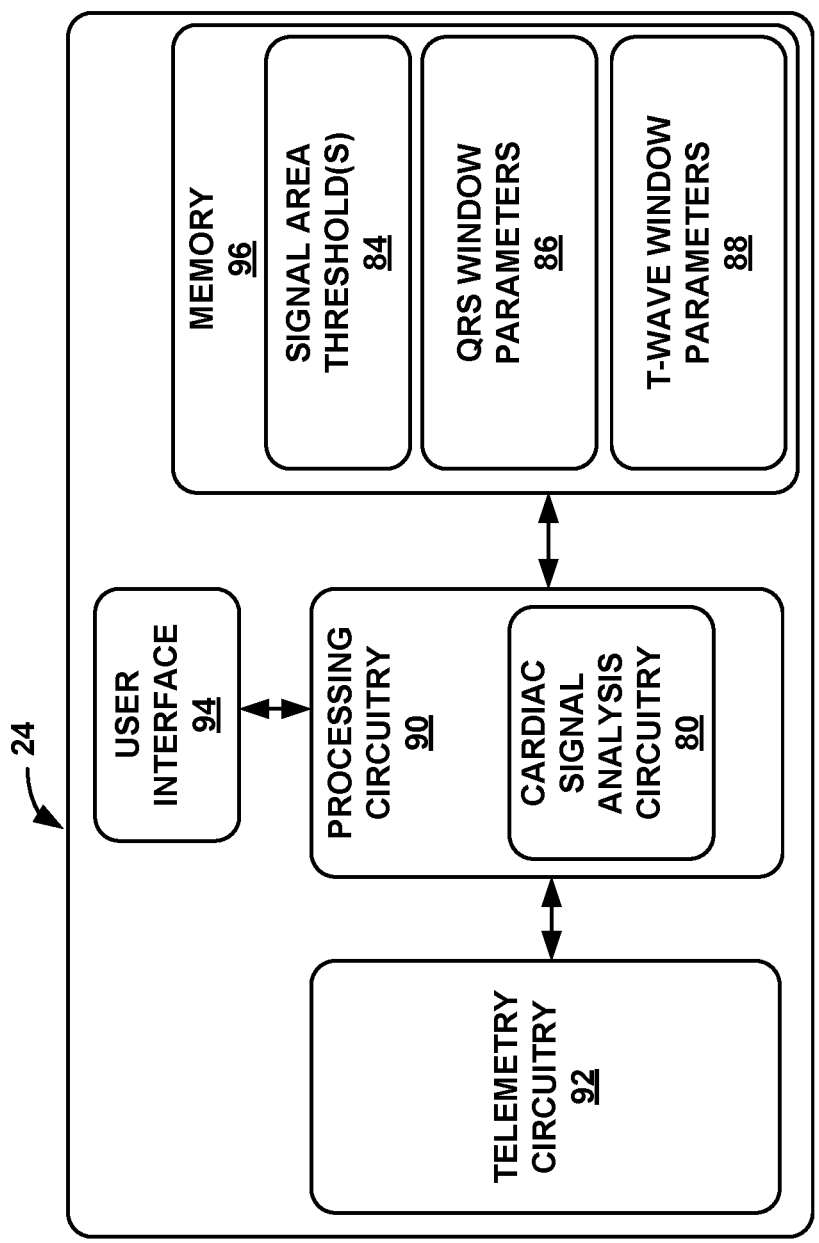
FIG. 4 is a block diagram illustrating an example configuration of an external device, which may be used with an IMD to identify one or more parameters of the cardiac EGM.

FIG. 4 is a block diagram illustrating an example configuration of external device 24, which may be used with IMD 16 to identify one or more parameters of the cardiac EGM. As illustrated in FIG. 4, external device 24 may include a processing circuitry 90, a memory 96, a telemetry circuitry 92, a user interface 94, and a cardiac signal analysis circuitry 80. External device 24 is an example of an external computing device that communicates with an IMD to perform the techniques for identifying one or more parameters of the cardiac EGM of this disclosure.

Processing circuitry 90 stores and retrieves information and instructions to and from memory 96. Processing circuitry 90 may include a microprocessor, a microcontroller, a DSP, an ASIC, an FPGA, or other equivalent discrete or integrated logic circuitry. Accordingly, processing circuitry 90 may include any suitable structure, whether in hardware, software, firmware or any combination thereof, to perform the functions ascribed herein to processing circuitry 90.

Memory 92 may include program instructions that, when executed by processing circuitry 90 and/or cardiac signal analysis circuitry 80, cause the processor and/or cardiac signal analysis circuitry to perform any of the functions attributed to them herein. Memory 96 may also include instructions for operating user interface 94 and telemetry circuitry 92. Memory 96 may include any volatile or nonvolatile memory such as RAM, ROM, EEPROM or flash memory. Memory 96 may also include a removable memory portion that may be used to provide memory updates or increases in memory capacities. A removable memory may also allow sensitive patient data to be removed before external device 24 is used by, or for, a different patient.

Telemetry circuitry 92 receives data from IMD 16 and may provide program instructions from processing circuitry 90 to IMD 16. In various examples, telemetry circuitry 92 includes any of a variety of circuitry known to facilitate wireless, e.g., radio-frequency or inductive, communication with IMD 16. In some examples, processing circuitry 90 receives indications from IMD 16 that a variance of QT intervals of the cardiac EGM of patient 14 is above a threshold variance value, thus indicating an arrhythmia. Processing circuitry 90 may present indications that the arrhythmia is present to a user, e.g., a physician, surgeon, or other clinician, via user interface 94. User interface 94 may also allow the user to view and change signal area thresholds 84, QRS window parameters 86, and T-wave window parameters 88. As illustrated in FIG. 4, memory 96 may store signal area thresholds 84, QRS window parameters 86, and T-wave window parameters 88. In other examples, memory 96 may store data not illustrated in FIG. 4.

In other examples, as illustrated in FIG. 4, external device 24 includes cardiac signal analysis circuitry 80, and cardiac signal analysis circuitry 80 and external device 24 are configured to perform the techniques for identifying parameters of cardiac EGMs substantially as described above with respect to IMD 16 and FIG. 3. For example, external device 24 may receive a cardiac EGM from IMD 16 via telemetry circuitry 92, and processing circuitry 90 may process the cardiac EGM to determine a plurality of QT intervals of the cardiac EGM using the techniques described with respect to FIG. 3. Additionally, or alternatively, the cardiac EGM may be partially processed by IMD 16 and partially processed by external device 24 (e.g., the QRS start and T-wave end times are determined by IMD 16 and the variance of the plurality of QT intervals is determined by external device 24).

User interface 94 includes a display (not shown), such as an LCD or LED display or other type of screen, to present any indications or information described herein for the techniques for identifying parameters of the cardiac signal according to this disclosure. In addition, user interface 94 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processing circuitry 90 of external device 24 and provide input. The input may include, for example, instructions to control IMD 16, external device 24, and cardiac signal analysis circuitry 80 in the performance of the techniques for identifying parameters of the cardiac signal according to this disclosure. In some examples, the display (not shown) of external device 24 may be a touch screen that allows the user to provide input directly to the user interface shown on the display. The user may use a stylus or a finger to provide input to the display. In other examples, user interface 94 additionally or alternatively includes audio circuitry for providing audible instructions or sounds to a user and/or receiving voice commands from the user.

Processing circuitry 90 and cardiac signal analysis circuitry 80 may be incorporated in a single processing unit. Cardiac signal analysis circuitry 80 may be a component of or a module executed by processing circuitry 90.

In some examples, a system for identifying arrhythmias includes any of a variety of networked external computing devices, such as servers, external devices, and client computing devices coupled via a network. Such systems may be implemented, in some aspects, with general network technology and functionality similar to that provide by the Medtronic CareLink® Network developed by Medtronic, Inc., of Minneapolis, Minn. In such examples, any one or more external computing devices of such a system may include cardiac signal analysis circuitry or may otherwise individually or collectively perform any of the techniques identifying parameters of the cardiac signal described herein.

Figure 5:
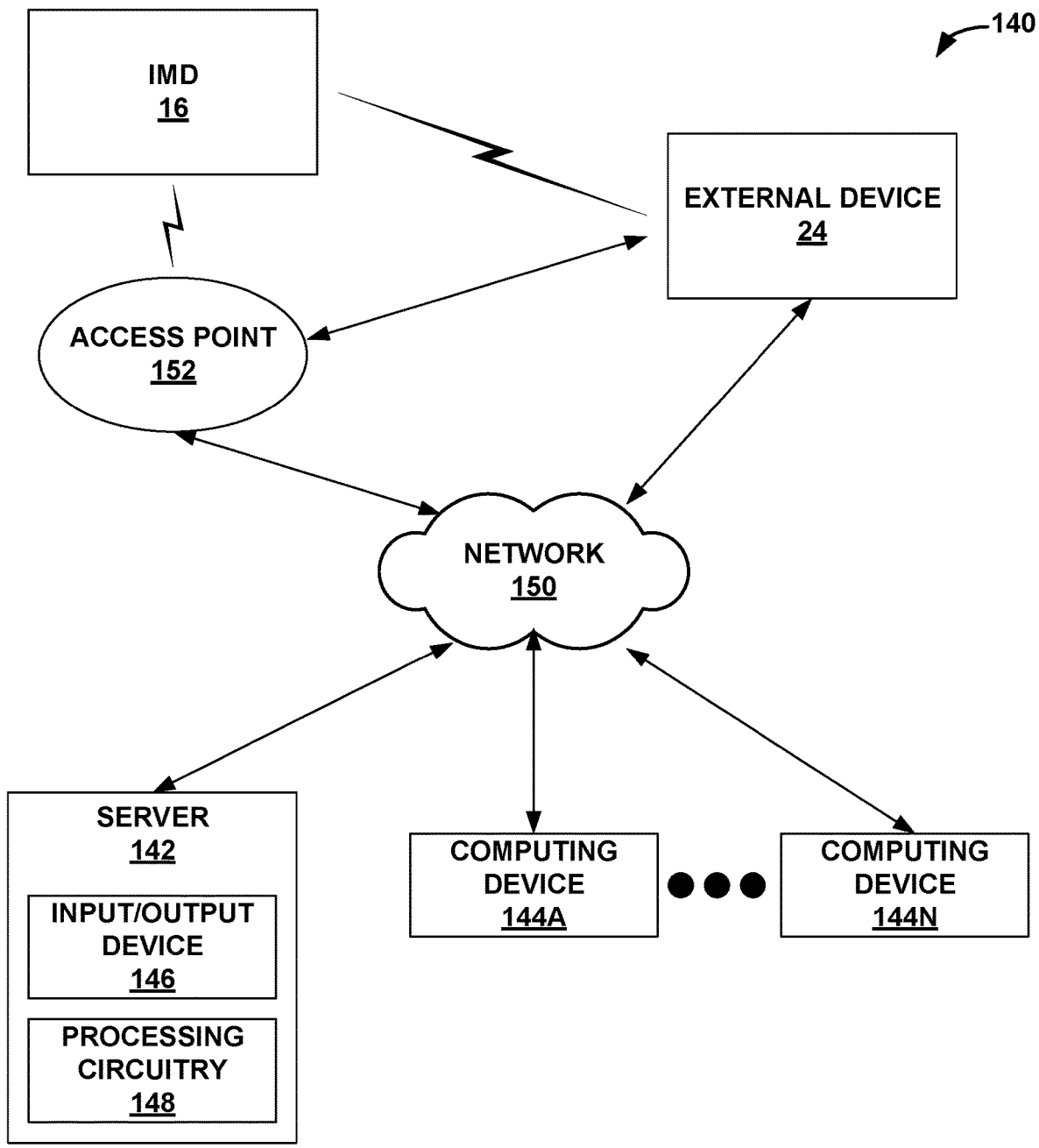
FIG. 5 is a block diagram illustrating a system that includes an external device, such as a server, and one or more computing devices that are coupled to an IMD and an external device via a network, in accordance with one or more aspects of this disclosure.

FIG. 5 is a block diagram illustrating a system 140 that includes an external device 142, such as a server, and one or more computing devices 144A-144N that are coupled to IMD 16 and external device 24 via a network 150, according to one example. In this example, IMD 16 uses communication circuitry to communicate with external device 24 via a first wireless connection and communicates with an access point 152 via a second wireless connection. In the example of FIG. 5, access point 152, external device 24, server 142, and computing devices 144A-144N are interconnected, and able to communicate with each other, through network 150. In some cases, one or more of access point 152, external device 24, external device 142, and computing devices 144A-144N may be coupled to network 150 through one or more wireless connections. IMD 16, external device 24, external device 152, and computing devices 144A-144N may each comprise one or more processing circuitries, such as one or more microprocessors, DSPs, ASICs, FPGAs, programmable logic circuitry, or the like, that may perform various functions and operations, such as those described herein.

Access point 152 may comprise a device that connects to network 150 via any of a variety of connections, such as telephone dial-up, digital subscriber line (DSL), or cable modem connections. In other examples, access point 152 may be coupled to network 150 through different forms of connections, including wired or wireless connections. In some examples, access point 152 may communicate with external device 24 and/or IMD 16. Access point 152 may be co-located with patient 14 (e.g., within the same room or within the same site as patient 14) or may be remotely located from patient 14. For example, access point 152 may be a home monitor located in the patient's home or is portable for carrying with patient 14.

During operation, IMD 16 may collect, measure, and store various forms of diagnostic data. For example, IMD 16 may collect cardiac EGM and motion signal data. In certain cases, IMD 16 may directly analyze collected diagnostic data and generate any corresponding reports or alerts. In some cases, however, IMD 16 may send diagnostic data to external device 24, access point 152, and/or external device 142, either wirelessly or via access point 152 and network 150, for remote processing and analysis. For example, IMD 16 may send external device 24 data that indicates whether an arrhythmia is imminent in patient 14. External device 24 may generate reports or alerts after analyzing the data.

In another example, IMD 16 may provide external device 142 with collected EGM and motion signal data, system integrity indications, and any other relevant physiological or system data via access point 152 and network 150. External device 142 includes one or more processing circuitries 148. In some cases, external device 142 may request such data, and in some cases, IMD 16 may automatically or periodically provide such data to external device 142. Upon receipt of the diagnostic data via input/output device 146, external device 142 can analyze the data and generate reports or alerts.

In one example, external device 142 may comprise a secure storage site for information that has been collected from IMD 16 and/or external device 24. In this example, network 150 may comprise an Internet network; and trained professionals, such as clinicians, may use computing devices 144A-144N to securely access stored data on external device 142. For example, the trained professionals may need to enter usernames and passwords to access the stored information on external device 142. In one embodiment, external device 142 may be a Medtronic CareLink® server provided by Medtronic plc of Dublin, Ireland.

In some examples, processing circuitry and memory of one or more of access point 152, server 142, or computing devices 144, e.g., processing circuitry 148 and memory of server 142, may be configured to provide some or all the functionality ascribed to processing circuitry and memory of IMD 16. For example, processing circuitry 148 of server 142 may determine an end of a QRS complex and an end of a T-wave of a cardiac EGM signal received at server 142. Additionally, or alternatively, server 142 may determine other parameters of the cardiac EGM. In response to determining parameters of the cardiac EGM, server 142 may deliver instructions to IMD 16 via network 150 and access point 152 and/or external device 24 to deliver therapy to patient 14.

Figure 6:
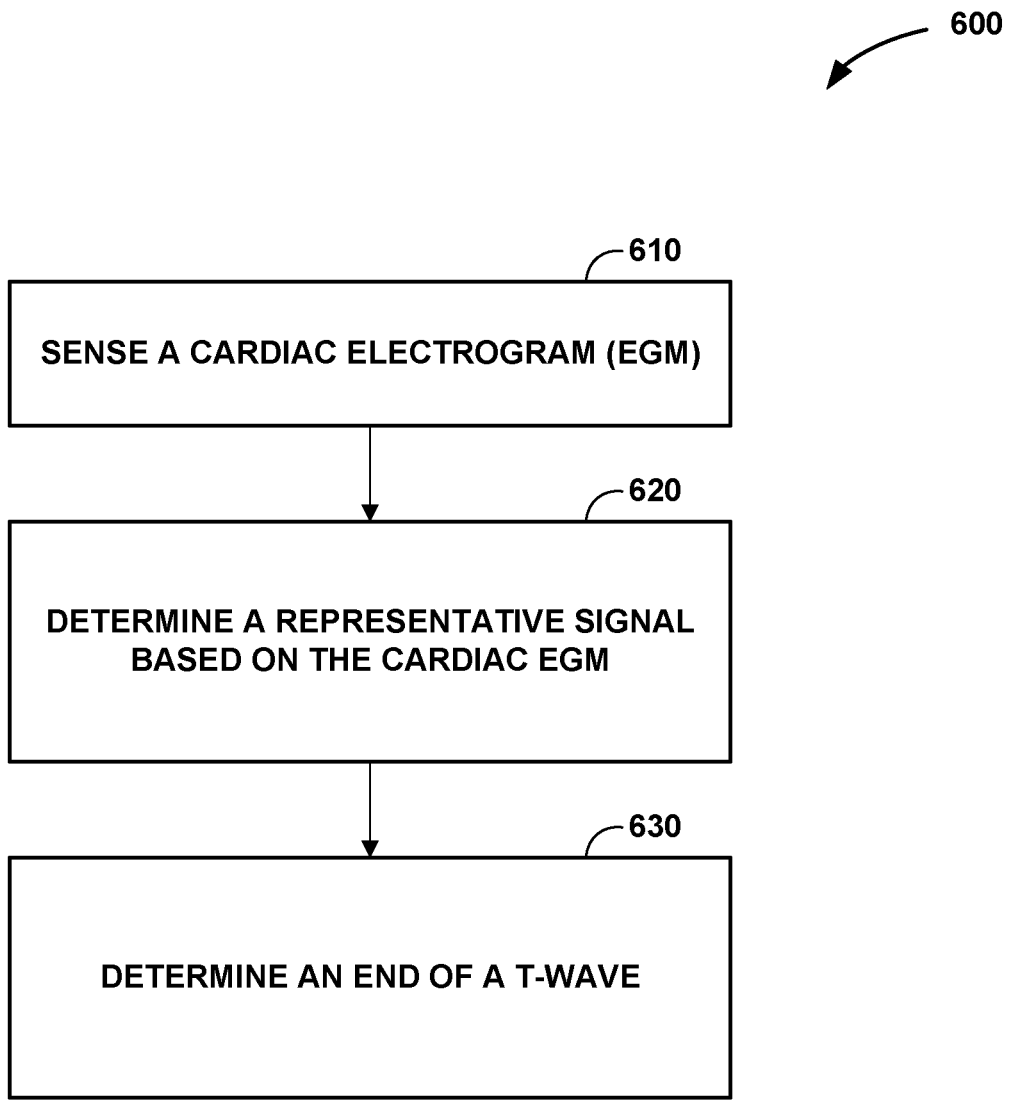
FIG. 6 is a flow diagram illustrating a first example method of determining a parameter of the cardiac EGM according to the techniques of this disclosure.

FIG. 6 is a flow diagram illustrating a first example method 600 of determining a parameter of the cardiac EGM according to the techniques of this disclosure. According to the example method of FIG. 6, a cardiac EGM is sensed (610). In one example, IMD 16 senses the cardiac EGM. As described herein, IMD 16 may include leads 18, 20, and 22 having electrodes 40, 42, 44-48, 50, 62, and 66. Additionally, housing 8 of IMD 116 may include electrode 4. Any combination of these electrodes may be configured to sense the cardiac EGM. Furthermore, any combination of processing circuitry 70 of IMD 16 and processing circuitry 90 of external device 24 may be configured to receive the sensed cardiac EGM. Subsequently, cardiac signal analysis circuitry 80 determines a representative signal based on the cardiac EGM (620). In one example, the representative signal defines a single polarity. Additionally, an end of a T-wave of the cardiac EGM may be determined, e.g., by cardiac signal analysis circuitry 80 (630). In one example, cardiac signal analysis circuitry 80 determines the end of the T-wave based on an area under the representative signal.

Figure 7:
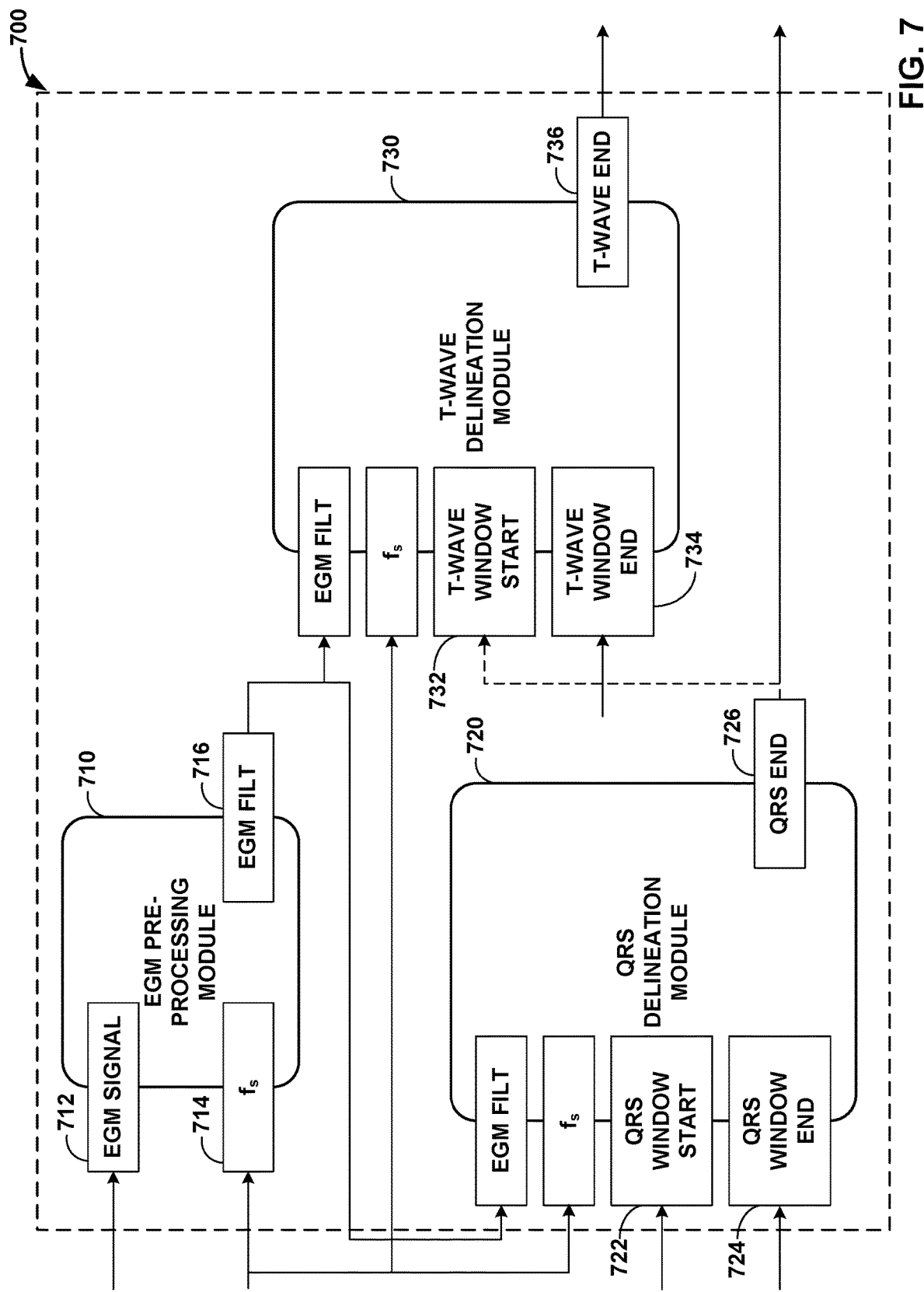
FIG. 7 is a block diagram illustrating example cardiac signal analysis circuitry that may be used to identify one or more parameters of the cardiac EGM according to the techniques of this disclosure.

FIG. 7 is a block diagram illustrating example cardiac signal analysis circuitry 700 that may be used to identify one or more parameters of the cardiac EGM according to the techniques of this disclosure. Cardiac signal analysis circuitry 700 may be an example of cardiac signal analysis circuitry 80 of FIG. 3 or FIG. 4. Cardiac signal analysis circuitry 700 may include EGM pre-processing module 710, EGM signal 712, sampling rate 714, filtered EGM signal 716, QRS delineation module 720, QRS window start time 722, QRS window end time 724, QRS complex end time 726, T-wave delineation module 730, T-wave window start time 732, T-wave window end time 734, and T-wave end time 736. EGM pre-processing module 710, QRS delineation module 720, and T-wave delineation module 730 may be implemented within one or more microprocessors, DSPs, ASICs, FPGAs, or any other equivalent integrated or discrete logic QRS circuitry, as well as any combinations of such components. The term "module" may generally refer to any of the foregoing logic circuitry, alone or in combination with other logic circuitry, or any other equivalent circuitry, and alone or in combination with other digital or analog circuitry. Although the example illustrated in FIG. 7 describes analysis of a cardiac EGM signal sensed by implantable electrodes, the techniques described herein may be used for analysis of other cardiac signals, such as ECGs recorded by external electrodes.

EGM pre-processing module 710 may be configured to receive EGM signal 712 sensed by sensing circuitry 76 via electrodes of IMD 16. EGM signal 712 may represent a cardiac EGM signal including noise from various sources. Pre-processing module 710 may be configured to sample EGM signal 712 at sampling rate 714, producing a discrete EGM signal which may be modified using signal processing techniques described herein. In on example, EGM pre-processing module 710 may include a Butterworth filter defining a band-pass filter having a frequency range extending from 1 Hertz to 10 Hertz. Hence, low frequency noise and high frequency noise may be filtered out of the EGM signal by EGM pre-processing block 710. Examples of noise may include respiration activity, muscle activity, gastrointestinal activity, and noise from other systems in the body. Other examples of noise may include 60 Hertz noise, white noise, or other external noise at any frequency from external sources such as medical equipment or other machinery. Butterworth filters are infinite impulse response (IIR) filters that may be designed with a flat frequency response (e.g., the signal is attenuated equally among frequencies not passed by the filter). Additionally, or alternatively, EGM pre-processing module 710 may include any combination of IIR filters, finite impulse response (FIR) filters, high-pass filters, low-pass filters, notch filters, Chebyshev filters, elliptic filters, Bessel filters, Gaussian filters, Linkwitz-Riley filters, or the like.

EGM pre-processing module 710 may produce filtered EGM signal 716. Since filters of EGM pre-processing module 710 are configured to remove noise from EGM signal 712, filtered EGM signal 716 may accentuate one or more features of a cardiac EGM signal previously obscured in EGM signal 712. For example, events such as P-waves, QRS complexes, and T-waves may be more visible in filtered EGM signal 316 than in EGM signal 712. Hence, parameters of a cardiac EGM may be more detectable in filtered EGM signal 716 than in EGM signal 712.

QRS delineation module 720 may receive filtered EGM signal 716 from EGM pre-processing module 710. Additionally, QRS delineation module 720 may sample filtered EGM signal 716 at sampling rate 714. QRS delineation module 720 may be configured to output QRS complex end time 726, the output representing a time in which a detected QRS complex concludes in the cardiac EGM signal. Initially, QRS delineation module 720 may set a QRS window indicative of a period of time in which a QRS complex is expected to end in a future portion of the cardiac EGM signal. For example, QRS delineation module 720 may detect an R-wave in filtered EGM signal 716 or receive an indication of an R-wave detection by other circuitry of IMD 16. Subsequently, QRS delineation module may set the QRS window beginning at QRS window start time 722 and extending to QRS window end time 724. In one example, QRS window start time 722 occurs 10 milliseconds following the detected R-wave, and QRS window end time 724 occurs 150 milliseconds following the detected R-wave. In other examples, QRS window start time 722 and QRS window end time 724 may include other values. QRS delineation module 720 may eliminate (e.g., "blank") all portions of filtered EGM signal 716 outside of the QRS window.

After QRS delineation module 720 blanks filtered EGM 716 signal outside the QRS window, QRS delineation module 720 may calculate a gradient of filtered EGM signal 716 inside the QRS window (e.g., calculate the slope of filtered EGM signal 716 at each point throughout the QRS window). The gradient may be a real-time derivative calculation. In some examples, QRS delineation module 720 may define a representative signal as the gradient of filtered EGM signal 716. In other examples, QRS delineation module 720 may amplify the gradient of filtered EGM signal 716, creating the representative signal of the QRS complex. In other examples, QRS delineation module 720 may amplify the gradient of filtered EGM signal 716 by calculating an exponential (e.g., square, cube, or the like) of the gradient. The representative signal of the QRS complex may include a single polarity, meaning the polarity of the representative signal does not change throughout the QRS window. For example, the representative signal may include entirely negative or entirely positive values, however the representative signal does not alternate between positive and negative values.

QRS delineation module 720 may determine QRS complex end time 726, the output representing a time that a QRS complex in the cardiac EGM of the patient concludes. In calculating QRS complex end time 726, QRS delineation module 720 may evaluate an area under the representative signal of the QRS complex. For example, QRS delineation module 720 may determine the end of the QRS complex as an earliest determined time in which the area under the representative signal of the QRS complex is greater than or equal to a threshold portion of a total area under the representative signal of the QRS complex. The area under the representative signal of the QRS complex may be evaluated at each point along the representative signal. In one example, the threshold portion of the total area under the representative signal is 0.9.

Filtered EGM signal 716 may define a discrete signal having a plurality of data points spaced at sampling rate 714. Hence, the representative signal of the QRS complex may also define a discrete signal, and QRS delineation module 720 may compute the area under the representative signal at each data point of the plurality of data points. In one example, the area of any portion of the representative signal within the QRS window may be computed by performing a summation of data points beginning with a data point at the start of the QRS window and ending with a data point indicating an end of the respective portion of the representative signal of the QRS complex.

T-wave delineation module 730 may receive filtered EGM signal 716 from EGM pre-processing module 710. As T-wave delineation module 730 receives filtered EGM signal 716, the module may sample filtered EGM signal 716 at sampling rate 714. T-wave delineation module 730 may be configured to output T-wave end time 736. In particular, T-wave end time 736 represents a time in which a T-wave concludes in the cardiac EGM signal. Like QRS delineation module 720, T-wave delineation module 730 may set time windows. For example, T-wave delineation module 730 may set a T-wave window, the T-wave window indicative of a period of time in which a T-wave is expected to end in a future portion of the cardiac EGM signal. For example, T-wave delineation module 730 may detect an R-wave in filtered EGM signal 716. Subsequently, T-wave delineation module 730 may set the T-wave window beginning at T-wave window start time 732 and extending to T-wave window end time 734. In one example, T-wave window start time 732 occurs at QRS complex end time 726 calculated by QRS delineation module 720, and T-wave window end time 734 occurs 700 milliseconds following the detected R-wave. In other examples, T-wave window start time 732 and T-wave end time 734 may include other values. T-wave delineation module 730 may eliminate (e.g., "blank") all portions of filtered EGM signal 716 outside of the T-wave window.

After T-wave delineation module 730 blanks filtered EGM signal 716 outside the T-wave window, T-wave delineation module 730 may calculate a gradient of filtered EGM signal 716 inside the T-wave window (e.g., calculate the slope of filtered EGM signal 716 at each point throughout the T-wave window). The gradient may be a real-time derivative calculation. In some examples, T-wave delineation module 730 may define a representative signal of the T-wave as the gradient of filtered EGM signal 716. In other examples, T-wave delineation module 730 may amplify the gradient of filtered EGM signal 716, creating the representative signal of the T-wave. In other examples, T-wave delineation module 730 may amplify the gradient of filtered EGM signal 716 by calculating an exponential (e.g., square, cube, or the like) of the gradient. The representative signal of the T-wave may include a single polarity, meaning the polarity of the representative signal does not change throughout the T-wave window. For example, the representative signal may include entirely negative or entirely positive values, however the representative signal does not alternate between positive and negative values.

T-wave delineation module 730 may determine T-wave end time 736. In calculating T-wave end time 736, T-wave delineation module 730 may be configured to evaluate an area under the representative signal of the T-wave. For example, T-wave delineation module 730 may determine the end of the T-wave as an earliest determined time in which the area under the representative signal of the T-wave is greater than or equal to a threshold portion of a total area under the representative signal of the T-wave. The area under the representative signal of the T-wave may be evaluated at each point along the representative signal. In one example, the threshold portion of the total area under the representative signal is 0.6. The representative signal of the T-wave may be a discrete signal, and an area under any portion of the representative signal may be determined by performing a summation of all data points within the respective portion of the representative signal.

Figure 8:
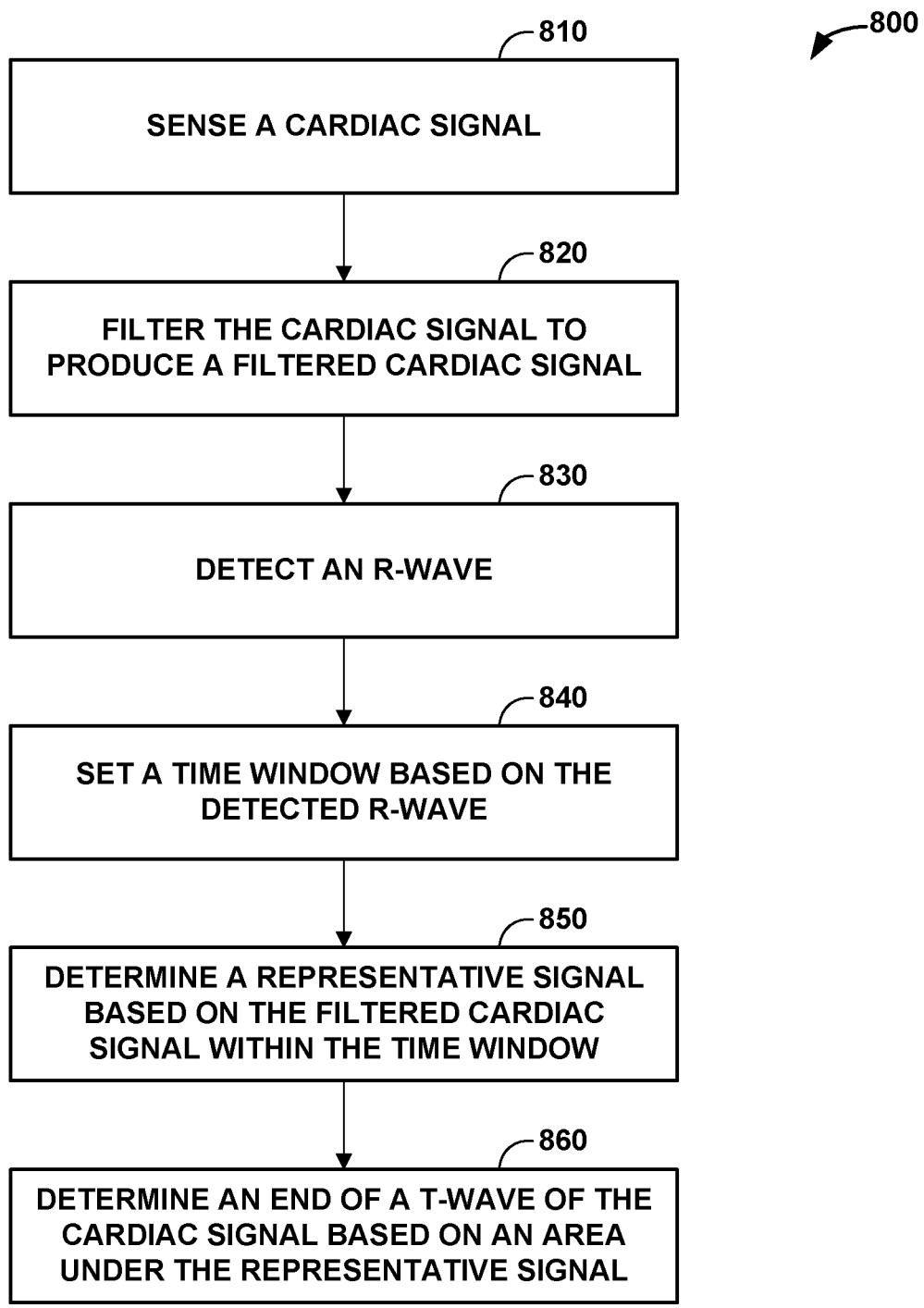
FIG. 8 is a flow diagram illustrating a second example method of determining a parameter of a cardiac signal according to the techniques of this disclosure.

FIG. 8 is a flow diagram illustrating a second example method 800 of determining a parameter of a cardiac signal according to the techniques of this disclosure. According to the example of FIG. 8, a cardiac signal is sensed (810). In some examples, the cardiac signal may be a cardiac EGM sensed by an IMD, such as IMD 16. In other examples, the cardiac signal may be an ECG sensed by electrodes of external devices, such as smart watches, fitness monitors, mobile devices, Holter monitors, wearable defibrillators, or the like. The cardiac signal is filtered to produce a filtered cardiac signal (820). An R-wave is detected (830) and a time window is set based on the detected R-wave (840). In one example, the time window starts at a first time relative to the detected R-wave and ends at a second time relative to the detected R-wave. A representative signal is determined signal based on the filtered cardiac signal within the time window (850) and an end of a T-wave of the cardiac signal is determined based on an area under the representative signal (860).

In one example, IMD 16 senses the cardiac EGM, filters the EGM, detects the R-wave, sets the time window, determines the representative signal, and determines the end of the T-wave. As described herein, IMD 16 may include leads 18, 20, and 22 having electrodes 40, 42, 44-48, 50, 62, and 66. Additionally, or alternatively, other devices such as external device 24 or server 142 may perform any combination of the steps of FIG. 8.

Figure 9:
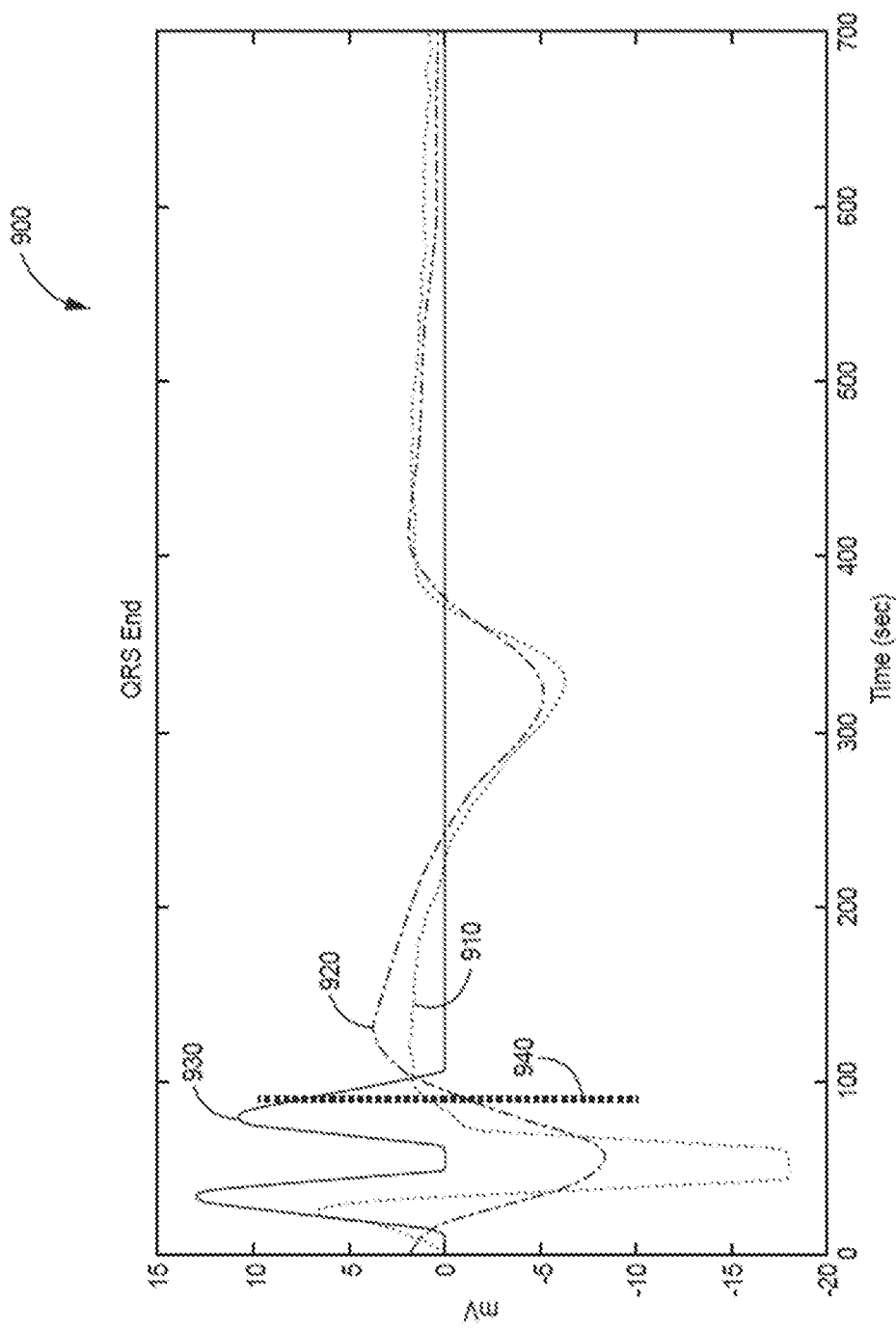
FIG. 9 is a voltage/time graph illustrating a QRS end time determined by an IMD, according to the techniques of this disclosure.

FIG. 9 is a voltage/time graph 900 illustrating QRS complex end time 940 determined by IMD 16, according to the techniques of this disclosure. Voltage/time graph 900 also illustrates cardiac EGM signal 910, filtered EGM signal 920, representative signal 930, and QRS end time 940. EGM signal 910 may be an example of EGM signal 712 of FIG. 7, Filtered EGM signal 920 may be an example of filtered EGM signal 716 of FIG. 7, and QRS complex end time 940 may be an example of QRS complex end time 726 of FIG. 7.

In the example illustrated in FIG. 9, cardiac EGM signal 910 is sensed by IMD 16 via one or more electrodes and sensing circuitry 76. Cardiac EGM signal 910 is filtered to determine filtered EGM signal 920, and representative signal 930 is determined based on filtered EGM signal 920. In one example, representative signal 930 is based on a QRS window based on a detected R-wave in cardiac EGM signal 910. The QRS window starts at a first time relative to the detected R-wave and ends at a second time relative to the detected R-wave. Representative signal 930, having a single polarity, may be defined by an a gradient of filtered EGM signal 920 within the QRS window. Additionally, or alternatively, representative signal 930 may be defined by an amplification of the gradient of filtered EGM signal 920 within the QRS window. QRS complex end time 940 may be calculated based on an earliest determined time in which the area under representative signal 930 is greater than or equal to a threshold portion of a total area under representative signal 930. As illustrated in FIG. 9, QRS complex end time 940 is located at a fraction of the total duration of representative signal 930, however QRS complex end time 940 is an accurate representation of the end of the QRS complex of cardiac EGM signal 910.

Figure 10:
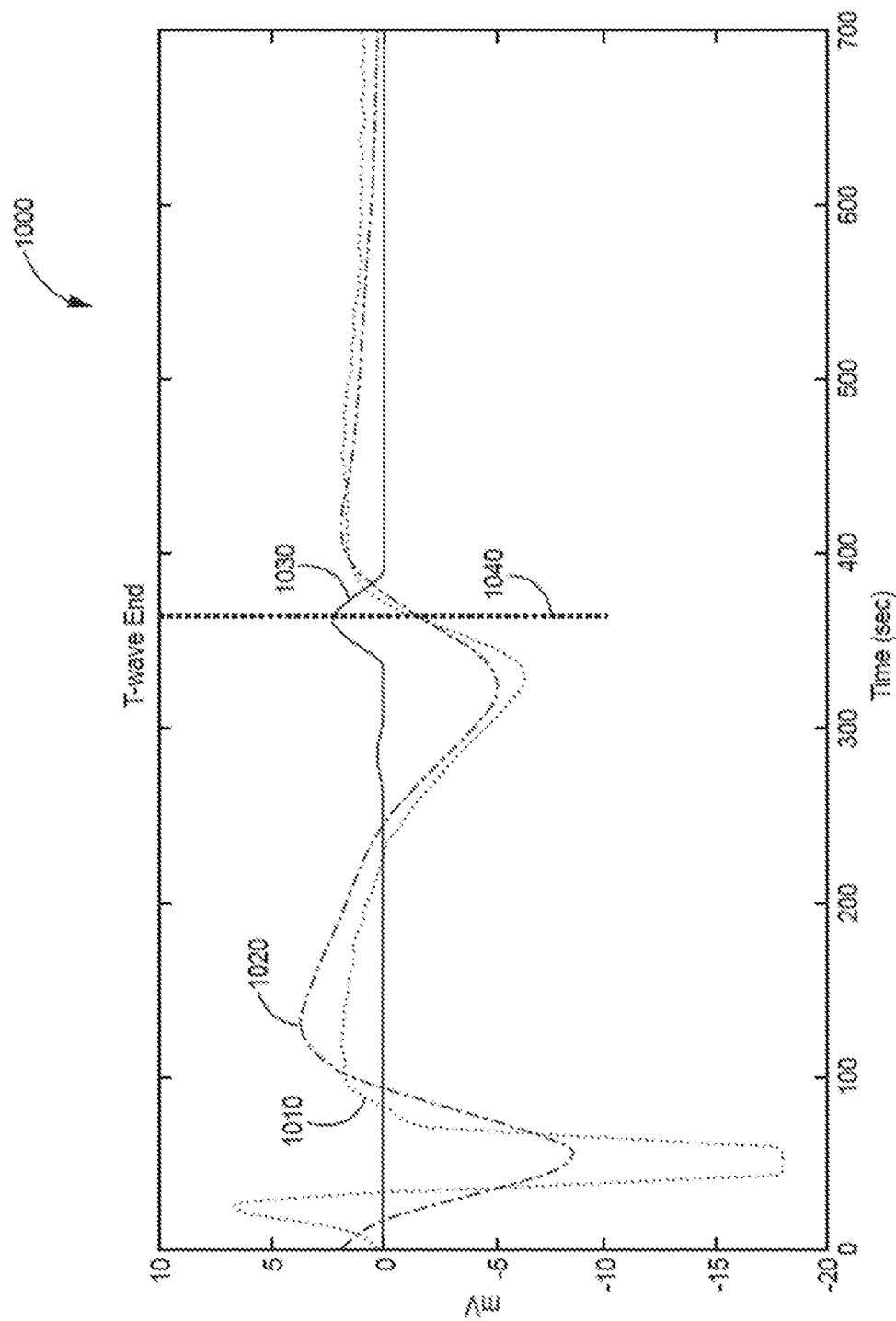
FIG. 10 is a voltage/time graph illustrating a T-wave end time determined by an IMD, according to the techniques of this disclosure.

FIG. 10 is a voltage/time graph 1000 illustrating T-wave end time 1040 determined by IMD 16, according to the techniques of this disclosure. Voltage/time graph 1000 also illustrates cardiac EGM signal 1010, filtered EGM signal 1020, representative signal 1030, and QRS end time 1040. EGM signal 1010 may be an example of EGM signal 712 of FIG. 7, Filtered EGM signal 1020 may be an example of filtered EGM signal 716 of FIG. 7, and T-wave end time 1040 may be an example of T-wave end time 736 of FIG. 7.

Cardiac EGM signal 1010 may be filtered to produce filtered EGM signal 1020. Subsequently, a T-wave window may be set, the T-wave window beginning at a first time relative to a detected R-wave and ending at a second time relative to the detected R-wave. In one example, the first time is a QRS complex end time, such as QRS complex end time 940 of FIG. 9. Representative signal 1030, having a single polarity, may be defined by a gradient of filtered EGM signal 1020 within the T-wave window. Additionally, or alternatively, representative signal 1030 may be defined by an amplification of the gradient of filtered EGM signal 1020. The T-wave window may be different than the QRS window of FIG. 9, therefore representative signal 1030 may be different than representative signal 930 of FIG. 9. T-wave end time 1040 may be calculated based on an earliest determined time in which the area under representative signal 1030 is greater than or equal to a threshold portion of a total area under representative signal 1030. As illustrated in FIG. 10, T-wave end time 1040 is located at a fraction of the total duration of representative signal 1030, however T-wave end time 1040 is an accurate representation of the end of the T-wave of cardiac EGM signal 910.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a non-transitory computer-readable storage medium such as RAM, ROM, NVRAM, EEPROM, FLASH memory, magnetic media, optical media, or the like. The instructions may be executed to support one or more aspects of the functionality described in this disclosure.

Various examples have been described. These and other examples are within the scope of the following claims.

What is claimed is:

1. A device comprising:
one or more electrodes;
processing circuitry configured to:
    receive, from the one or more electrodes, a cardiac signal;
    determine a representative signal based on the cardiac signal, the representative signal having a single polarity, wherein the representative signal comprises a gradient of the cardiac signal; and
    determine one or more features of the cardiac signal based on an area under the representative signal.

2. The device of claim 1, wherein to determine the one or more features of the cardiac signal, the processing circuitry is configured to determine one or more features of a QRS complex of the cardiac signal.

3. The device of claim 2, wherein to determine the one or more features of the QRS complex, the processing circuitry is configured to determine a start of the QRS complex, determine an end of the QRS complex, determine a duration of the QRS complex, or any combination thereof.

4. The device of claim 2, wherein to determine the one or more features of the QRS complex, the processing circuitry is configured to determine an end of the QRS complex based on the area under the representative signal.

5. The device of claim 4, wherein the end of the QRS complex is an earliest determined time in which the area under the representative signal is greater than or equal to a portion of a total area under the representative signal.

6. The device of claim 5, wherein the portion of the total area under the representative signal is 0.9.

7. The device of claim 1, wherein to determine the one or more features of the cardiac signal, the processing circuitry is configured to determine one or more features of a P-wave of the cardiac signal.

8. The device of claim 1, wherein the representative signal is a first representative signal, and wherein the processing circuitry is further configured to:
determine a second representative signal based on the cardiac signal, the second representative signal having a single polarity, wherein the second representative signal comprises a gradient of the cardiac signal; and
determine one or more features of the cardiac signal based on an area under the second representative signal.

9. The device of claim 8, wherein the second representative signal comprises an exponential of the gradient of the cardiac signal.

10. The device of claim 8, wherein to determine the one or more features of the cardiac signal based on an area under the second representative signal, the processing circuitry is configured to determine one or more features of a T-wave of the cardiac signal based on an area under the second representative signal.

11. The device of claim 10, wherein to determine the one or more features of a T-wave of the cardiac signal based on the area under the second representative signal, the processing circuitry is configured to determine a start of the T-wave, determine an end of the T-wave, determine a duration of the T-wave, or any combination thereof.

12. The device of claim 10, wherein to determine the one or more features of the T-wave, the processing circuitry is configured to determine an end of the T-wave based on an area under the second representative signal.

13. The device of claim 12, wherein the end of the T-wave is an earliest determined time in which the area under the second representative signal is greater than or equal to a portion of a total area under the second representative signal.

14. The device of claim 13, wherein the portion of the total area under the second representative signal is 0.6.

15. The device of claim 8,
wherein to determine the one or more features of the cardiac signal based on the area under the first representative signal, the processing circuitry is configured to determine an end of a QRS complex of the cardiac signal, and
wherein the processing circuitry is configured to determine the second representative signal based on a time window of the cardiac signal after the end of the QRS complex, wherein the time window starts at a first time and ends at a second time.

16. The device of claim 15, wherein the processing circuitry is further configured to detect an R-wave of the cardiac signal, wherein the first time is the end of the QRS complex, and wherein the second time is 700 milliseconds after the detected R-wave.

17. The device of claim 15, wherein the processing circuitry is configured to:
determine a heart rate based on the cardiac signal;
decrease a length of the time window when the heart rate increases; and
increase the length of the time window when the heart rate decreases.

18. The device of claim 1, wherein the device, including the one or more electrodes, is configured to be implanted in a patient, and wherein the cardiac signal comprises a cardiac electrogram.

19. A method comprising:
receiving, by processing circuitry from one or more electrodes, a cardiac signal;
determining, by the processing circuitry, a representative signal based on the cardiac signal, the representative signal having a single polarity, wherein the representative signal comprises a gradient of the cardiac signal; and
determining, by the processing circuitry, one or more features of the cardiac signal based on an area under the representative signal.

20. A non-transitory, computer-readable storage medium storing a set of instructions that, when executed, cause one or more processors to:
receive a cardiac signal;
determine a representative signal based on the cardiac signal, the representative signal having a single polarity, wherein the representative signal comprises a gradient of the cardiac signal; and
determine one or more features of the cardiac signal based on an area under the representative signal.

* * * * *